US007577232B2

(12) United States Patent
Tachibana et al.

(10) Patent No.: US 7,577,232 B2
(45) Date of Patent: Aug. 18, 2009

(54) MEDICAL X-RAY IMAGING APPARATUS AND X-RAY DETECTOR FOR USING THE SAME

(75) Inventors: Akifumi Tachibana, Kyoto (JP); Masanobu Yoshida, Kyoto (JP); Takahiro Yoshimura, Kyoto (JP); Masakazu Suzuki, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 11/407,504

(22) Filed: Apr. 20, 2006

(65) Prior Publication Data

US 2006/0256921 A1      Nov. 16, 2006

(30) Foreign Application Priority Data

Apr. 22, 2005    (JP)    ............................. 2005-125809

(51) Int. Cl.
*A61B 6/14*    (2006.01)
*H05G 1/58*    (2006.01)

(52) U.S. Cl. ........................... 378/39; 378/38; 378/116

(58) Field of Classification Search ............... 378/4–20, 378/38–40, 62, 98.8, 114–116, 147–149, 378/210, 168–170, 177–180, 191, 195, 181, 378/189

See application file for complete search history.

(56) References Cited

U.S. PATENT DOCUMENTS

| | | | | |
|---|---|---|---|---|
| 4,365,340 A | * | 12/1982 | Nishikawa et al. ............ 378/39 |
| 6,118,842 A | * | 9/2000 | Arai et al. ..................... 378/39 |
| 6,169,780 B1 | * | 1/2001 | Yoshimura et al. ............ 378/39 |
| 6,863,440 B2 | * | 3/2005 | Sildve et al. ................. 378/208 |
| 7,099,428 B2 | * | 8/2006 | Clinthorne et al. ............ 378/17 |
| 2001/0036246 A1 | * | 11/2001 | Graumann .................... 378/39 |
| 2002/0018543 A1 | * | 2/2002 | Danielsson ................ 378/98.8 |
| 2003/0215051 A1 | * | 11/2003 | Suzuki ......................... 378/19 |
| 2005/0117693 A1 | * | 6/2005 | Miyano ......................... 378/4 |
| 2005/0117696 A1 | * | 6/2005 | Suzuki et al. ................. 378/19 |
| 2006/0233301 A1 | * | 10/2006 | Erhardt et al. ................ 378/38 |
| 2006/0239400 A1 | * | 10/2006 | Sukovic et al. ................ 378/38 |
| 2008/0137802 A1 | * | 6/2008 | Suzuki et al. ................... 378/4 |

FOREIGN PATENT DOCUMENTS

| | | |
|---|---|---|
| JP | 7-275240 | 10/1995 |
| JP | 10-225455 | 8/1998 |

* cited by examiner

*Primary Examiner*—Edward J Glick
*Assistant Examiner*—Anastasia Midkiff
(74) *Attorney, Agent, or Firm*—William L. Androlia; H. Henry Koda

(57) ABSTRACT

An X-ray detector for use in a medical X-ray imaging apparatus comprising a rotary means rotatable relative to an object to be examined, an X-ray generator provided at one side of the rotary means, and an X-ray detecting portion provided at the other side of the rotary means so as to face the X-ray generator. The X-ray detector is provided in the X-ray detecting portion or is detachably mounted in the X-ray detecting portion, the X-ray detector is provided with an imaging portion comprised of a plane electric imaging means extending in a two-dimensional direction used for X-ray CT and has an imaging portion positioning means for moving up and down the imaging portion in the X-ray detector.

19 Claims, 33 Drawing Sheets

MEDICAL X-RAY IMAGING APPARATUS AND X-RAY DETECTOR FOR USING THE SAME

FIELD OF THE INVENTION

The present invention relates to a medical X-ray imaging apparatus, more specifically to an X-ray imaging apparatus capable of panoramic radiography and computer tomography (CT) for use in dentistry, otolaryngology, or other medical fields and an X-ray detector for using the apparatus.

PRIOR ART

The X-ray imaging apparatus capable of panoramic radiography and X-ray CT has been disclosed in JP-A-10-225455. In this prior art, a mode switching means selects a panoramic radiography mode and an X-ray CT mode to move an X-ray source and an X-ray imaging means according to the selected radiography mode, thereby obtaining X-ray images. JP-A-10-225455 discloses an X-ray imaging apparatus capable of panoramic radiography and X-ray CT by selecting the radiography mode so as to execute both radiographies by means of one apparatus.

SUMMARY OF THE INVENTION

According to JP-A-10-225455, one X-ray imaging apparatus can execute both panoramic radiography and X-ray CT by selecting the radiography mode. It uses a CCD sensor or a MOS sensor with a wide image receiving area by switching the image receiving area according to the radiography mode, and such sensors have been expensive. Further, either panoramic radiography or X-ray CT is not executed by selectively using two-dimensional sensors with different shape.

According to the present invention, an electric imaging means with relatively small and plane shape like a MOS sensor is designed to move up and down at an X-ray detecting portion so as to enlarge the imaging area for X-ray CT.

A CCD sensor and a MOS sensor with a large image receiving area used for an X-ray detector have cost performance problems because they are expensive. In dental or otolaryngologic diagnosis, a panoramic radiography is executed in advance and an interested area is determined for the region required to be examined in detail, and an X-ray CT is executed for the area, thereby conducting diagnosis. Panoramic radiography is executed in advance for the interested area required for X-ray CT, so that X-ray CT can be executed for a relatively small area.

The present invention is proposed in order to achieve the above mentioned objects.

According to the X-ray detector of the present invention, a patient is once positioned at an X-ray imaging apparatus, the height of rotary means is adjusted for the patient to execute panoramic radiography, and thereafter the height of plane electric imaging means for X-ray CT is minutely controlled without changing the position of patient for panoramic radiography. Therefore, a relatively small and plane shaped electric imaging means is moved up and down, thereby providing an X-ray detector capable of X-ray CT at low cost.

Further according to the X-ray detector of the present invention, the imaging portion positioning means is so constructed as to move up and down the imaging portion by a motor, so that the operator is not required to execute troublesome manual operations.

Further according to the X-ray detector of the present invention, the imaging portion positioning means can be moved up and down stepwisely relative to an objective imaging region which is clinically important like an upper jaw, a lower jaw, and a temporomandibular joint.

Further according to the X-ray detector of the present invention, an elongated electric imaging means is used for panoramic radiography and a plane electric imaging means extending in a two-dimensional direction but not having the height (length) of the elongated electric imaging means is used for X-ray CT, thereby eliminating an expensive large sheet of sensor and achieving panoramic radiography and X-ray CT.

Further according to the X-ray detector of the present invention, two different electric imaging means are arranged for one side of a substrate board, so that they can be switched and used according to the object of radiography.

Still further according to the X-ray detector of the present invention, a general-purpose electric imaging means with high performance can be used for radiography in the present invention.

According to the medical X-ray imaging apparatus with an imaging portion positioning means of the present invention, a patient is once positioned for the X-ray imaging apparatus, a rotary means is adjusted to the height of patient to execute panoramic radiography and the height of plane electric imaging means for X-ray CT is minutely controlled keeping the patient positioning for panoramic radiography Therefore, the X-ray imaging apparatus capable of X-ray CT is achieved at low cost by moving up and down a relatively small plane electric imaging means.

Further according to the X-ray imaging apparatus using the above-mentioned X-ray detector of the present invention, the X-ray detector is detachable to or fixed on the X-ray imaging apparatus, thereby reducing the cost by detachably exchanging the detector or integrating the detector to the X-ray imaging apparatus, if necessary.

Further according to the X-ray imaging apparatus using the above-mentioned X-ray detector of the present invention, the irradiating direction of X-ray beam from the X-ray generator can be varied up and down, thereby achieving an X-ray imaging apparatus without increasing the radiation exposure.

Further according to the X-ray imaging apparatus using the above-mentioned X-ray detector of the present invention, the X-ray detector is selectively used so as to switch into several kinds of radiography modes.

Further according to the X-ray imaging apparatus using the above-mentioned X-ray detector of the present invention, the elongated electric imaging means is used for panoramic radiography and the plane electric imaging means is used for X-ray CT, so that an expensive large sheet of sensor is not required.

Further according to the X-ray imaging apparatus of the present invention, the irradiation field is moved up and down by modifying or moving the slit without moving the imaging portion up and down, thereby achieving a simple structure.

Further according to the X-ray imaging apparatus of the present invention, panoramic radiography also becomes possible.

Further according to the X-ray imaging apparatus of the present invention, the rotary means can be controlled in two-dimensional directions defined by an X-axis direction and a Y-axis direction, so that the rotary means can be moved for X-ray CT while using an X-Y table of rotary means for panoramic radiography.

Further according to the X-ray imaging apparatus of the present invention, the height and angle of object to be examined which is once fixed can be minutely controlled.

Still further according to the X-ray imaging apparatus of the present invention, the rotary means can be moved up and down independent of an object holding means relative to a fixed patient, thereby increasing positioning variation.

BRIEF DESCRIPTION OF THE DRAWINGS

FIG. 17 explains the detail of the X-ray generator.

DETAILED DESCRIPTION OF THE INVENTION

Embodiment 1

Figure 1:
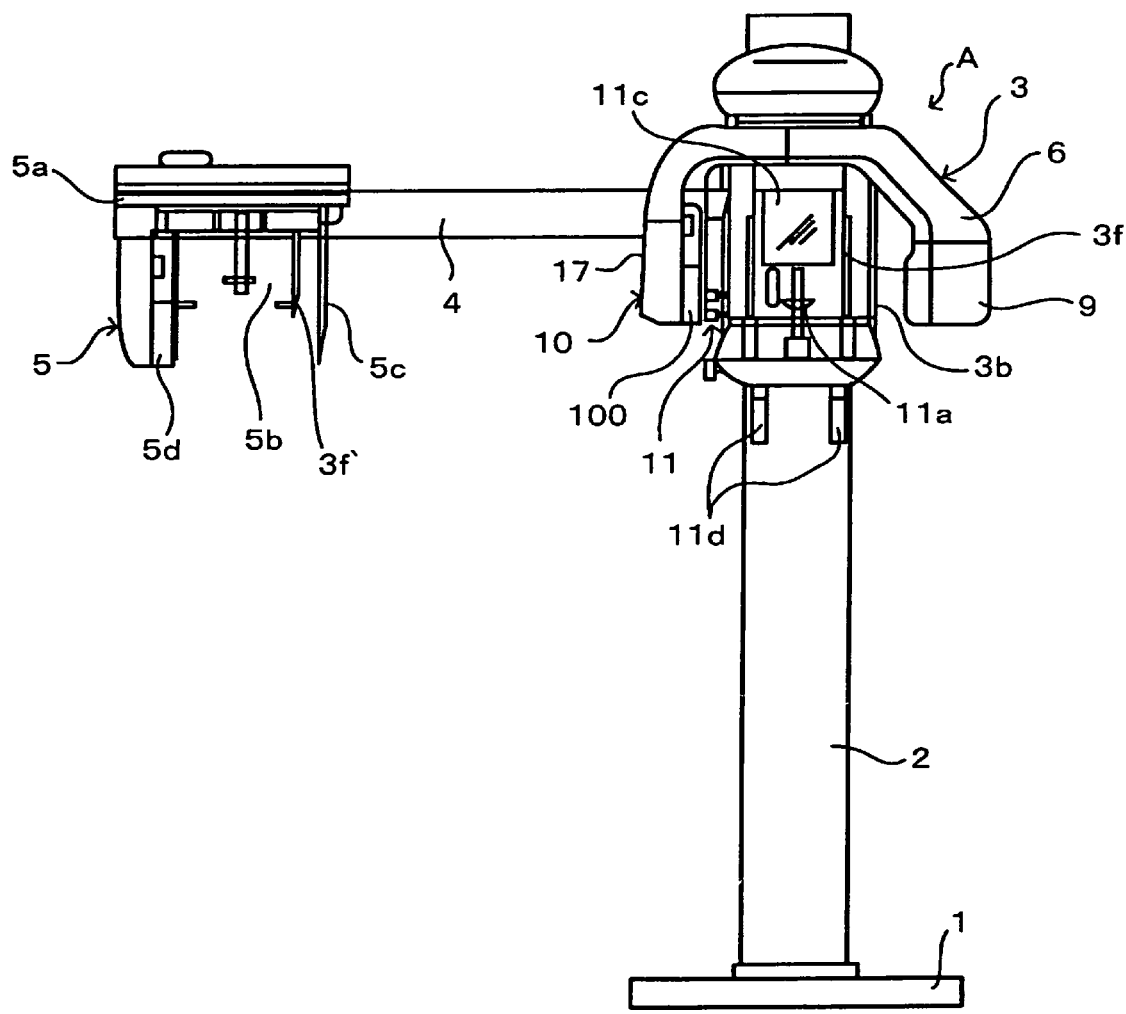
FIG. 1 shows a front view of a dental X-ray imaging apparatus as one example of a medical X-ray imaging apparatus of the present invention.
Figure 2:
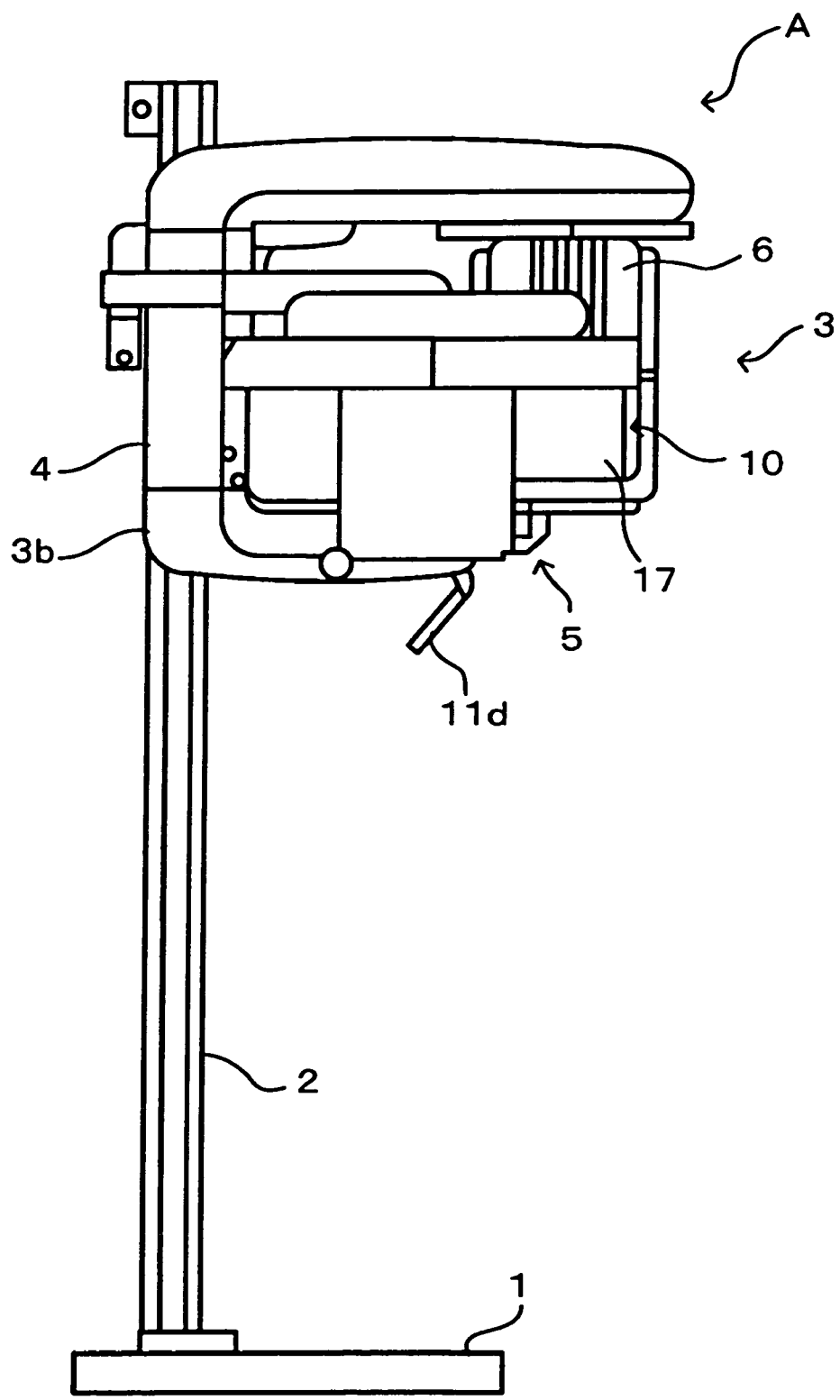
FIG. 2 is the side view of the apparatus of FIG. 1.
Figure 5:
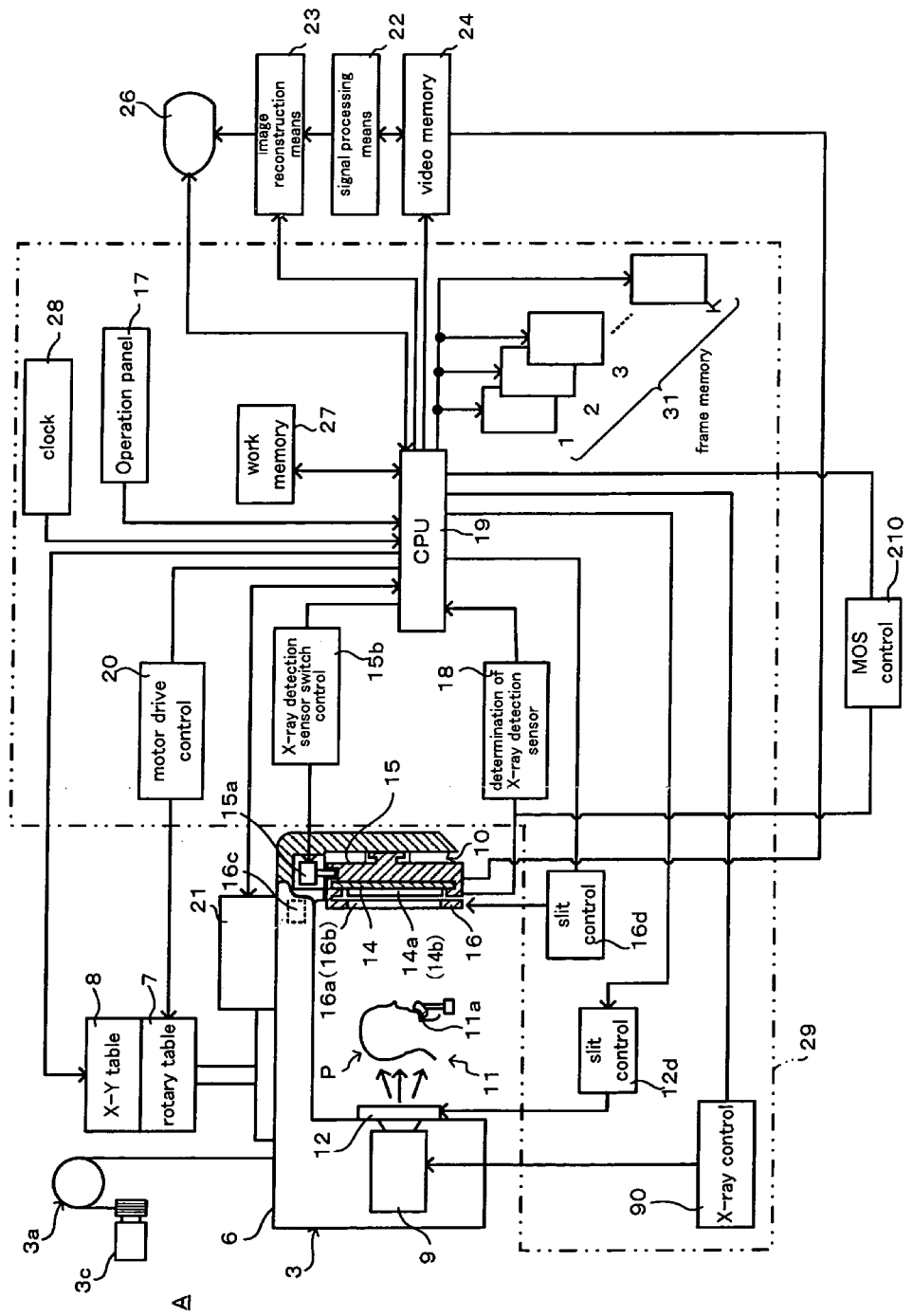
FIG. 5 shows the entire structure of the dental X-ray imaging apparatus.

A dental X-ray imaging apparatus A shown in FIG. 1, FIG. 2 and FIG. 5 is an X-ray imaging apparatus capable of panoramic radiography and X-ray CT in which a support pillar 2 is raised on a base board I provided on a floor and a main body 3 is supported for the support pillar 2 so as to move up and down via an elevating mechanism 3a with a motor 3c (refer to FIG. 5). An arm for cephalometric radiography 4 in horizontal direction is fixed with a C-shaped (seen from side) main frame (support) 3b of the main body of elevating mechanism 3 and a cephalometric radiography unit 5 is provided at the tip end of the arm 4. The cephalometric radiography unit 5 has a patient's head holding portion 5b (including an ear presser 3f and so on) at the lower surface of a base plate 5a rotatable around a vertical axis and has a first slit for cephalometric radiography 5c and an X-ray detecting portion 5d for cephalometric radiography so as to interpose the patient's head holding portion 5b. The main frame 3b supports a rotary arm 6 as a rotary means and the support pillar 2 is an elevating guide portion for guiding to move up and down the main frame 3b.

The rotary arm 6 (rotary means) of reverse concave shape is suspended and supported at the upper part of the main frame 3b to be rotatable horizontally or movable on a horizontal two-dimensional area or on a horizontal plane area by means of a rotary table 7 and an X-Y table 8 (see FIG. 5)-*included* in the main frame 3b.

The X-ray imaging apparatus A has a two-dimensional position control means for at least controlling position of the rotary means in two-dimensional directions defined by an X-axis direction and a Y-axis direction in three-dimensional axial directions defined by the X-axis normal to Z-axis, the Y-axis, and the Z-axis, where the Z-axis is defined as up and down direction of the imaging portion which will be described later.

Figure 3A:
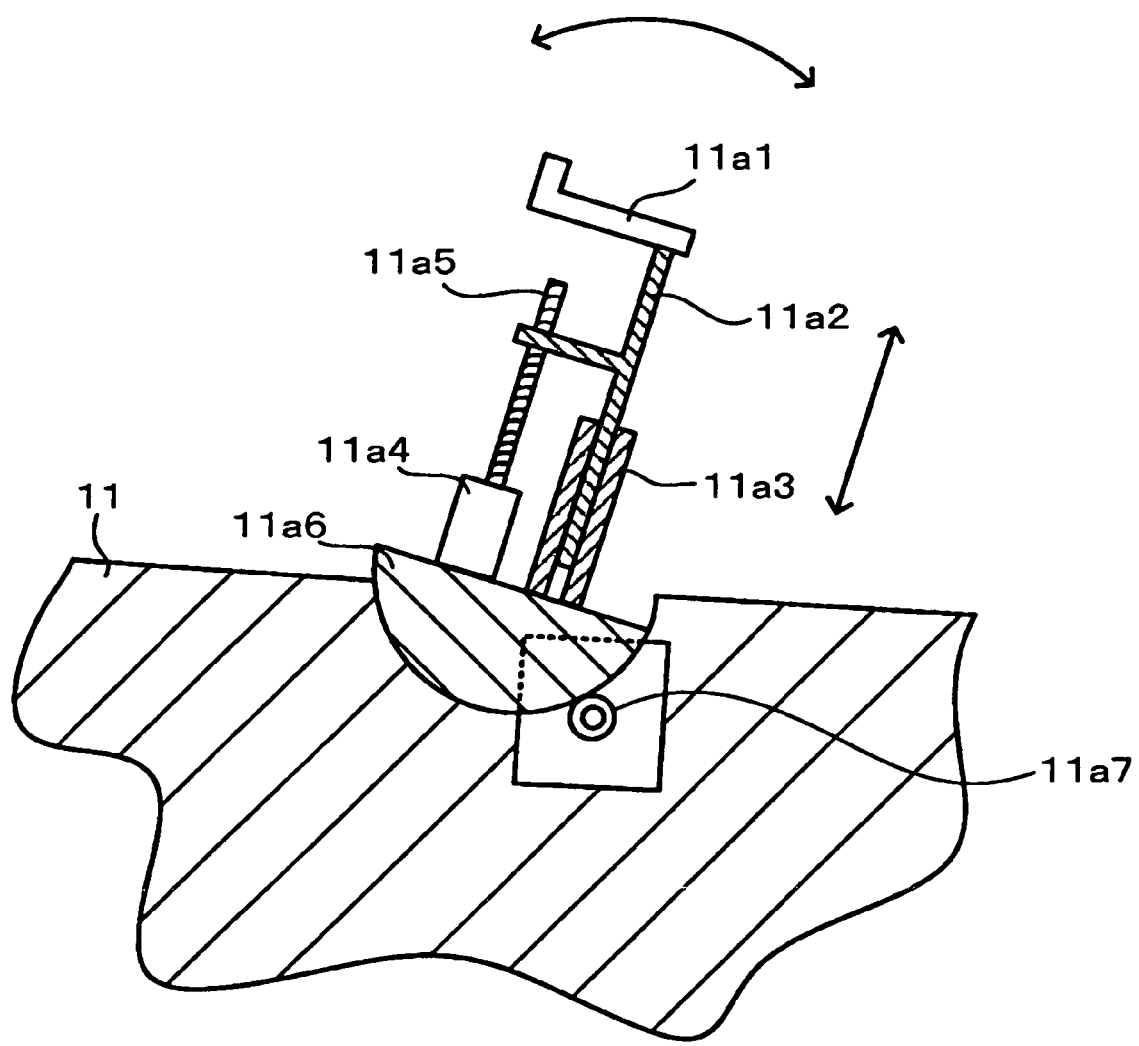
FIG. 3A is an explanatory view of a chin rest elevating means.

The rotary means is not limited to the shape of the rotary arm 6 shown in the figures and may be like a ring. An X-ray generator 9 is provided at one end (one side) of the rotary arm 6 and an X-ray detecting portion 10 is provided at the other end (other side) so as to face the X-ray generator 9. A head holding portion 11 for holding the head of patient P is formed between the X-ray generator 9 and the X-ray detecting portion 10 and is provided with a patient positioning member like a chin rest 11a. The head holding portion 11 functions as an object holding means for holding an object to be examined and the patient positioning member functions as an object fixing means for fixing the object to be examined. The object fixing means includes the ear presser 3f shown in FIG. 1 and a nasion presser for fixing the nasion of patient. The chin rest 11a is movable up and down or is able to tilt so as to be positioned according to the size of patient. FIG. 3A shows an embodiment in which the chin rest 11a is designed to be movable up and down or capable of tilting. A chin resting portion 11a1 for putting the chin of patient is fixed at the tip end of a bar-like member 11a2 to be guided with a guiding member 11a3 to be moved up and down by the action of a screw shaft 11a5 driven by a motor 11a4; The chin resting portion 11a1, the bar-like member 11a2, the guiding member 11a3, the motor 11a4, and the screw shaft 11a5 are mounted on a pedestal 11a6 and the chin rest 11a is entirely able to tilt when the pedestal 11a6 is guided by a guiding member (not shown) to be rotated relative to the head holding portion 11 by driving the motor 11a7. It may be of course constructed so as to be movable up and down or to be able to tilt. The bar-like member 11a2, the guiding member 11a3, the motor 11a4, the screw shaft 11a5, the pedestal 11a6, and the motor 11a7 function as an object shifting means for shifting the chin rest 11a capable of tilting and/or movable up and down relative to the main body of the head holding portion 11. According to such structure, the chin rest 11a is designed to be movable up and down and/or to be able to tilt, the tilt of irradiation beam relative to a horizontal plane can be controlled per a radiography region like an upper jaw, a lower jaw, a temporomandibular joint and so on and the regions apart up and down, such as a temporomandibular joint at an upper position and the tip end of lower jaw at a lower position, can be positioned at the center of irradiation field. The reference numeral 11d shows a handle which is held by a patient standing on the base board 1 and 11c shows a mirror.

The shifting structure of object fixing means may be in different ways.

Figure 3B:
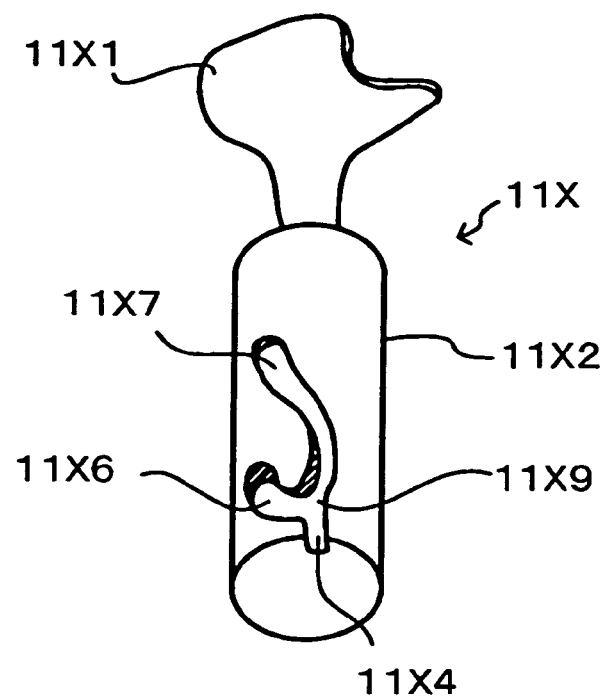
FIG. 3B is other explanatory view of a chin rest elevating means.
Figure 3B:
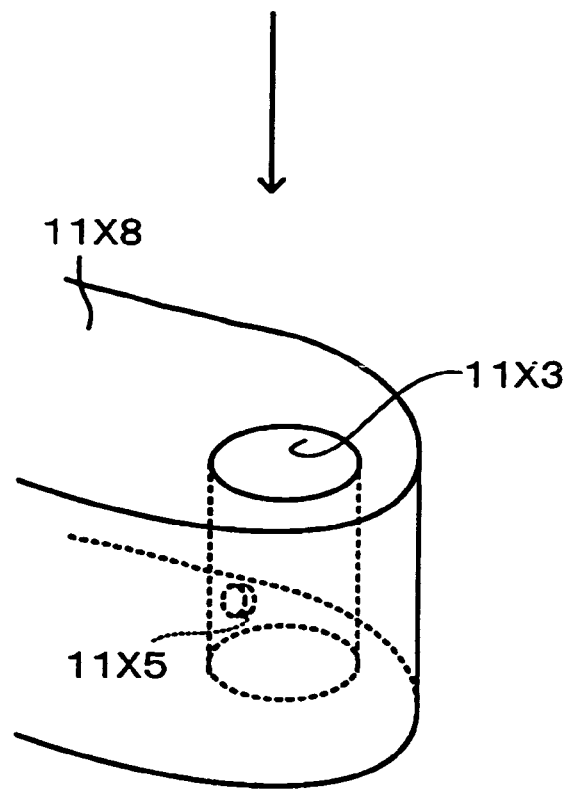

According to Japanese Utility Model Registration No. 3047733 proposed by the present inventors discloses an example for shifting an object fixing means like a chin rest as shown in FIG. 3B and the structure thereof is applicable to the present invention.

The chin rest 11x is comprised of a chin resting portion 11x1 for putting chin and a cylindrical attachment portion 11x2 connected with the chin resting portion 11x1 in FIG. 3B. The groove-like concave portion 11x4 formed at the cylindrical attachment portion 11x2 has a branch point 11x9, a first engaging concave (a first portion to be engaged) 11x6, and a second engaging concave (a second portion to be engaged) 11x7 and is designed such that a pin 11x5 projected to the inside of an attachment hole 11x3 of the tip end 11x8 of a lower frame is positioned so as to be manually engaged with either one of the first engaging concave (first portion to be engaged) 11x6 and the second engaging concave (second portion to be engaged) 11x7.

These groove-like concave 11x4, the first engaging concave (first portion to be engaged) 11x6, the second engaging concave (second portion to be engaged) 11x7, and the pin 11x5 correspond to the object shifting means of the present invention.

The structure of head holding portion 11 is detailed here. The head holding portion 11 goes up and down according to the size of patient relative to the support pillar 2 in the embodiment shown in FIG. 1. The holding portion for the patient with the chin rest 11a and the main frame 3b which moves up and down while guided by the support pillar 2 are integrally formed. Therefore, the X-ray generator 9 and the X-ray detecting portion 10 are designed to move up and down together with the head holding portion 11. However, the above-mentioned head holding portion 11 and the main frame 3b may be separately constructed so as to be independently shifted relative to the support pillar 2 respectively. On the other hand, the X-ray generator 9 may be shifted relative to the patient holding portion.

Figure 4A:
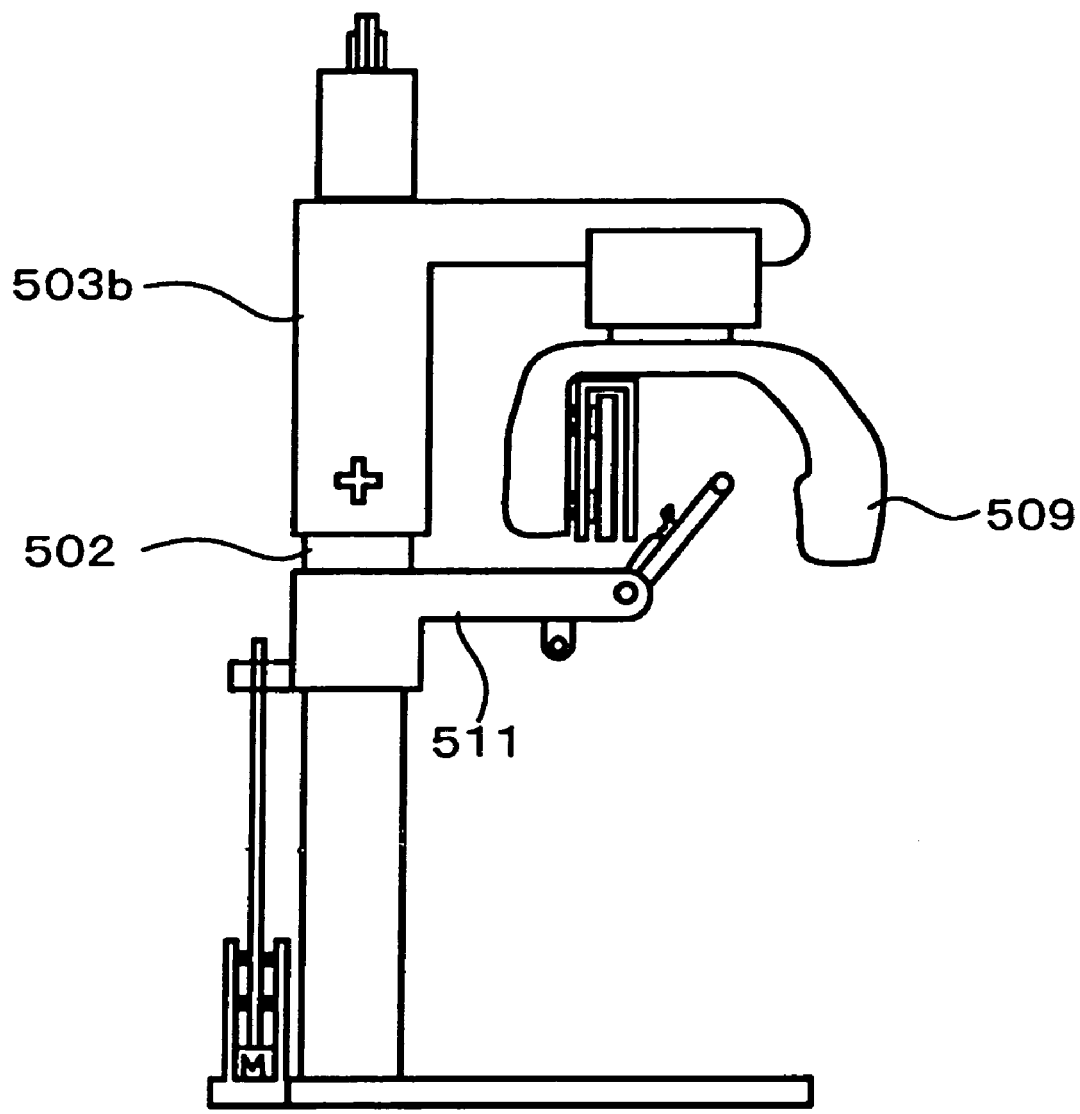
FIG. 4A and FIG. 4B show other embodiment of the medical X-ray imaging apparatus.
Figure 4B:
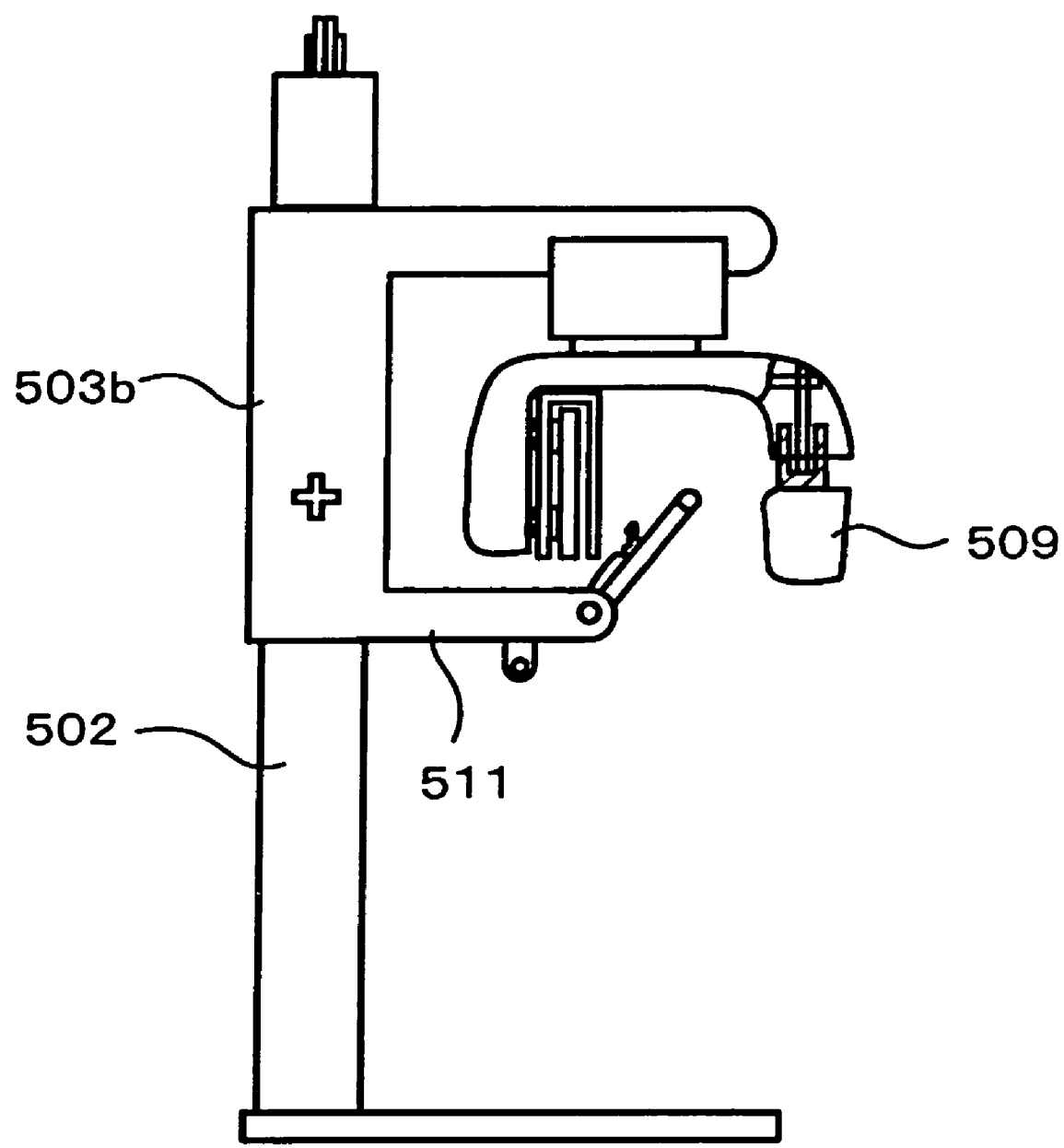

JP-A-7-275240 proposed by the present inventors discloses an embodiment in which a main body of elevating mechanism 503b (corresponds to a main frame 3b of the present invention) and a patient frame 511 (corresponds to the head holding portion 11 of the present invention) are separately constructed for the above-mentioned support pillar 502 as shown in FIG. 4A and an embodiment in which the X-ray generator 509 is shifted up and down relative to the patient frame 511 (the same as above) as shown in FIG. 4B. These structures of JP-A-7-275240 are applicable to the present invention.

In JP-A-7-275240, the object is to enlarge the area to be imaged, for example, to adjust the tilt of irradiation beam relative to a horizontal plane per a radiography region, and to adjust the position of the up-and-down apart regions, like a temporomandibular joint at an upper position and the tip end of a lower jaw at a lower position, at the center of the irradiation field. The structure of the chin rest 11a movable up and down or being able to tilt, the structure in which the patient holding portion and the elevating and shifting portion relative to the support pillar 502 are separately designed, and the structure for shifting the X-ray generator 9 up and down relative to the patient holding portion may be combined so as to execute more minute adjustment.

Figure 17A:
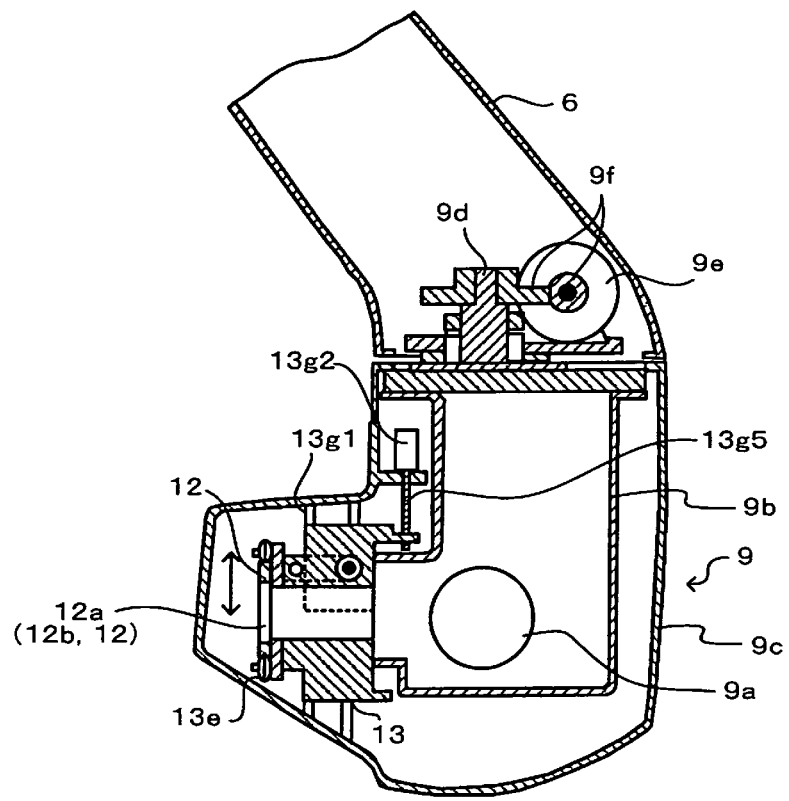
FIG. 17(a) is its vertical sectional view and FIG. 17(b) is its perspective view of the essential part.

The X-ray generator 9 is comprised of an X-ray tube 9a, an inner case 9b, and an outer case 9c including the X-ray tube 9a and is supported at one end of the rotary arm 6 via a vertical support shaft 9d as shown in FIG. 17. The vertical support shaft 9d is axially rotatable with a motor 9e and a gear 9f so as to rotate (swing) the X-ray generator 9 around the axial center of a vertical support shaft 9d. A support block 13 for a first slit plate 12 is fixed at an X-ray radiation port of the X-ray tube 9a and the first slit plate 12 is provided for the support block 13 so as to be movable in lateral direction.

The motor 13a for driving slit is fixed at one face of the support block 13 and the base of slit support rod 13c is screwed into a screw shaft 13b connected with an output shaft of the motor 13a. The tip end of guide bar 13d slidably supported with the support block 13 in the same direction of the screw shaft 13b is fixed to the slit support rod 13c. Accordingly, the slit support rod 13c is screwed in or out in lateral direction according to the axial rotation of the screw shaft 13b by driving the motor 13a. The first slit board 12 is fixed into the tip end of the slit support rod 13c and the upper edge and lower edge of the slit board 12 are interposed with plural rollers 13e attached to the support block 13, thereby smoothing the lateral movement of the slit board 12 according to the screwing in-and-out movement of the slit support rod 13c.

A wheel 13g4 is provided for the support block 13 and is guided with a guide rail 13g1 fixed into the outer case 9c in such a manner that the support block 13 entirely moves up and down by the action of a ball screw 13g5 driven by a motor 13g2 fixed into the outer case 9c. Driving the motor 13g2, the first slit board 12 moves up and down together with the support block 13 to change the irradiating direction of X-ray beam, so that the position of irradiation field is shifted up and down.

Figure 17B:
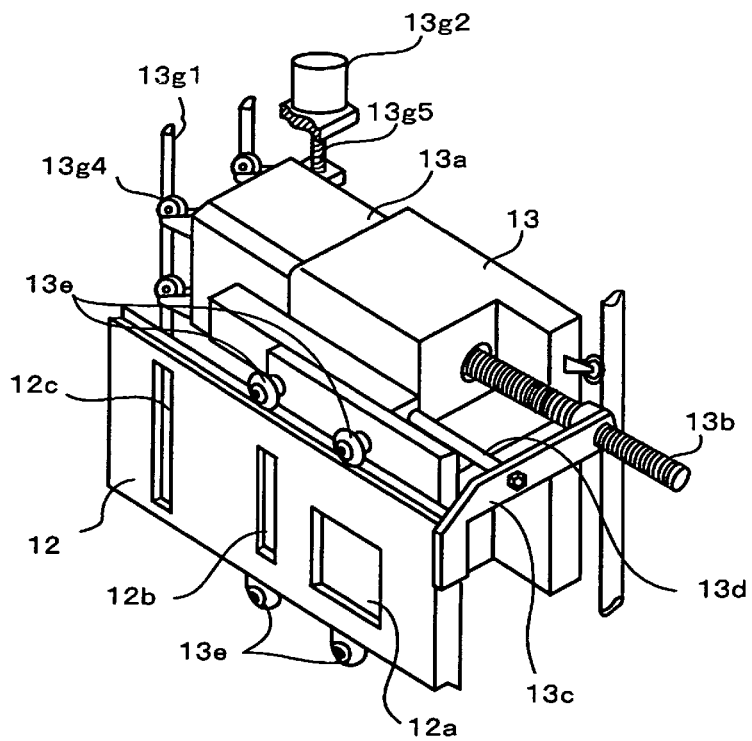

The first slit board 12 has a substantially rectangular (applicable to an X-ray detection sensor with the size of about 120 mm×120 mm) slit 12a which forms X-ray beam as X-ray conebeam for X-ray CT, a long (applicable to an X-ray detection sensor with the size of about 150 mm×6 mm) slit 12b for panoramic radiography, and a longer (applicable to an X-ray detection sensor with the size of about 225 mm×6 mm) slit 12c for cephalometric radiography which are arranged in parallel as shown in FIG. 17(b). Slit 12b and slit 12c form X-ray slit beam. When the motor 13a is driven according to radiography mode, these slits 12a, 12b and 12c are positioned at the X-ray radiation port respectively. In case of setting at cephalometric radiography mode, the slit 12c for cephalometric radiography is positioned and the X-ray generator 9 is driven to be swung by a motor 9e so as to direct X-ray beam into an X-ray detecting portion 5d for cephalometric radiography of the cephalometric radiography unit 5.

The X-ray detecting portion 10 shown in FIG. 5 has a sensor holder 15 for holding an X-ray detection sensor substrate 14 formed with two kinds of X-ray detection sensors (electric imaging means) 14a, 14b at the other end of the rotary arm 6 so as to be laterally movable with the motor 15a. The X-ray detection sensor substrate 14 has an output connector (not shown) for the X-ray detection sensors 14a, 14b respectively in such a manner that when the X-ray detecting portion 10 is attached via the sensor holder 15, the connector is designed to be connected with the input portion (not shown) formed at the X-ray detecting portion 10.

Figure 23A:
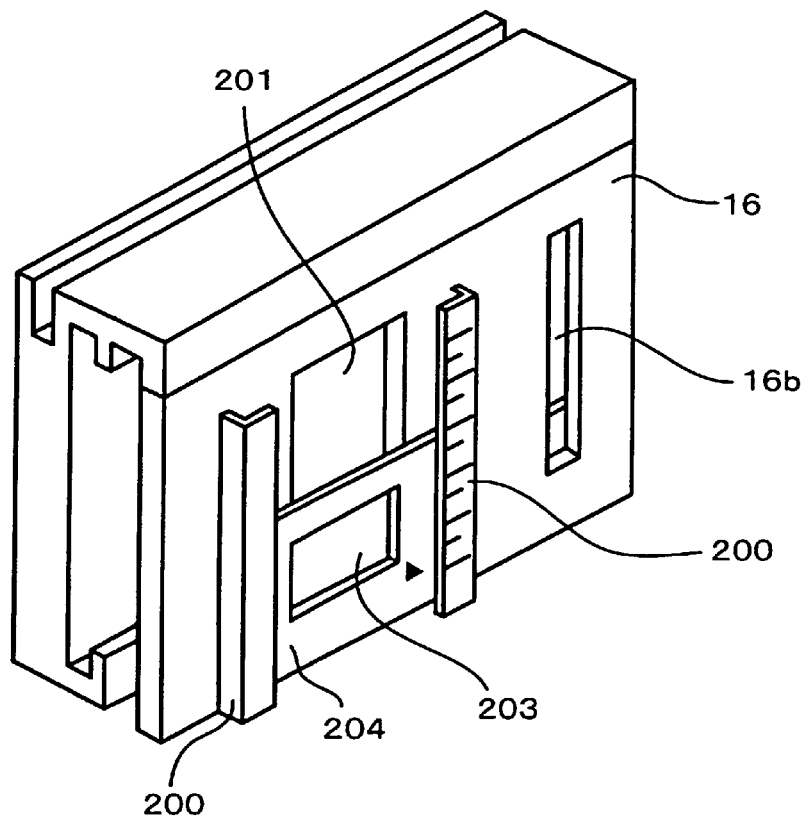
FIG. 23 is a vertical sectional view showing still other embodiment of an X-ray detecting portion.
Figure 23B:
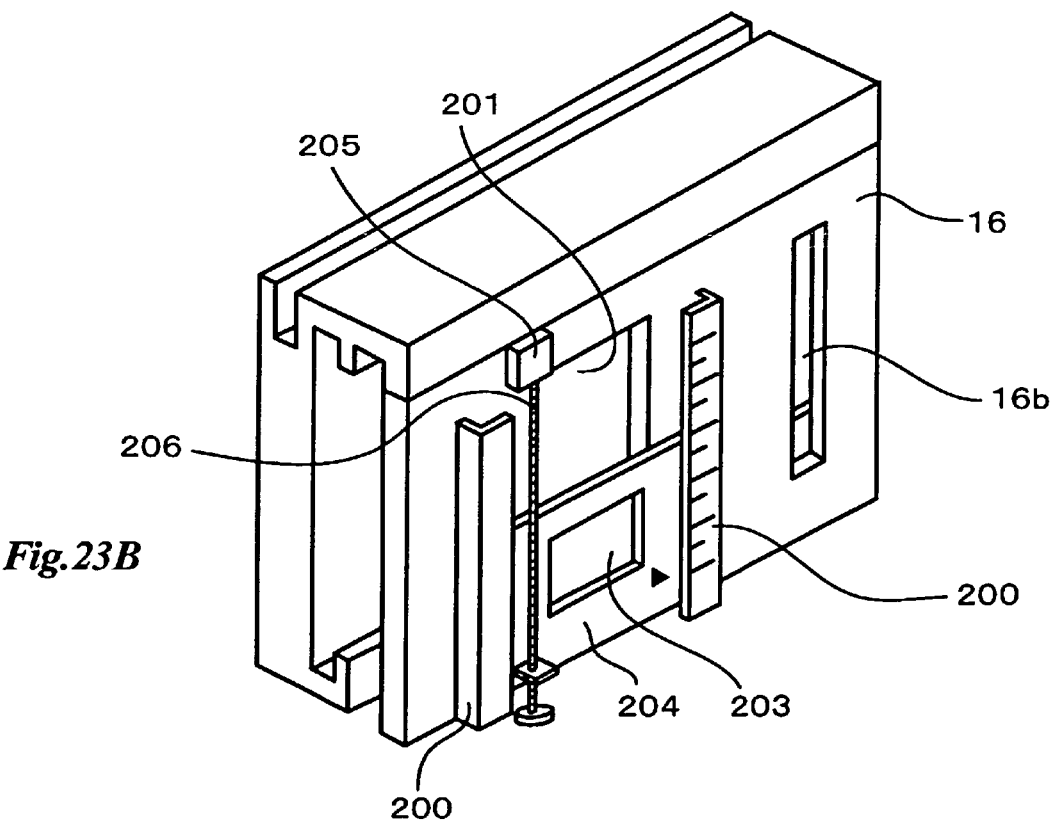

A second slit board 16 formed with two kinds of slits 16a, 16b, which are explained later, is provided in front of the X-ray detection sensor substrate 14 and is movable in lateral direction with a motor 16c. Accordingly, one of the X-ray detection sensors 14a, 14b is selectively set by driving the motor 15a and one of the slits 16a, 16b is selectively set according to the kinds of sensors 14a, 14b, namely according to radiography mode, by driving a motor 16c. Such an X-ray detection sensor substrate 14 and a second slit board 16 is detachably provided for the X-ray detecting portion 10 as a cassette unit 100 as shown in FIG. 1 and may be detachably provided for the X-ray detecting portion 5d for cephalometric radiography of the cephalometric radiography unit 5 to be commonly used. Further, a part of the second slit board 16 may be movable up and down, which is shown in FIG. 23 as an example. A part of the second slit board 16 is formed at a plane board 204 being a separate member. The plane board 204 has a rectangular slit 203 for the X-ray detection sensor 14a comprised of MOS, explained later. An opening 201 larger than the slit 203 is provided for the second slit board 16 and is provided behind the plane board 204. A guiding member 200 is provided at left and right of the opening 201 on the second slit board 16 to guide elevating of the plane board 204. The slit 203 is moved up and down according to the up-and-down movement of an imaging portion 300 comprised of the X-ray detection sensor 14a being MOS, which is explained later. FIG. 23A shows an embodiment of manual up-and-down movement and FIG. 23B shows an embodiment of automatic up-and-down movement with a screw 206 driven with a motor 205.

Figure 6:
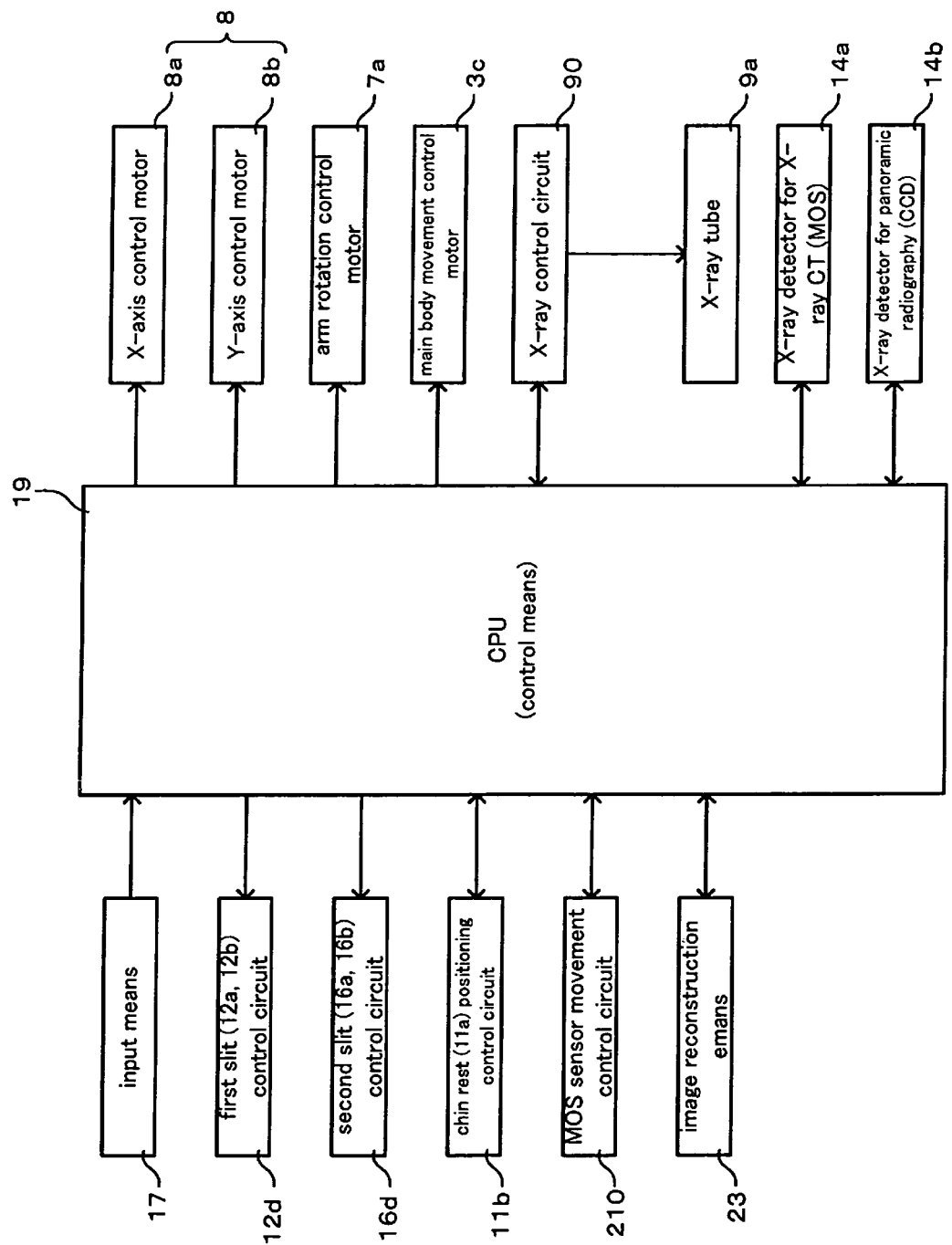
FIG. 6 shows a diagrammatic structural view of control block of the dental X-ray imaging apparatus.

Operation control of the above-mentioned dental X-ray imaging apparatus A is explained hereinafter further referring to FIG. 5 and FIG. 6. These figures explain panoramic radiography and X-ray CT, but cephalometric radiography is omitted. In case of executing panoramic radiography, when a panoramic radiography mode is selected on an operation panel (input means) 17, the elongated X-ray detection sensor 14b comprised of CCD on the X-ray detection sensor substrate 14 is positioned at the irradiation field of X-ray beam by driving the motor 15a as mentioned later. Further, the long slit 16b formed on the second slit board 16 is positioned in front of the X-ray detection sensor 14b by driving the motor 16c. The motor 15a is controlled to be driven by means of an X-ray detection sensor switching control circuit 15b and the motor 16c is controlled to be driven by a second slit control circuit 16d. The X-ray detection sensor substrate 14 has an IC chip (not shown) for discriminating two kinds of X-ray detection sensors 14a, 14b and the detected information is input into CPU 19 from the determination circuit 18 for the kinds of X-ray detection sensor, thereby determining which one of the X-ray detection sensor 14a, 14b is positioned.

In the X-ray generator 9, the motor 13a is controlled to be driven by a first slit control circuit 12d to set the slit 12b for panoramic radiography at an X-ray radiation port. The motor 3c for controlling up-and-down movement of the main body of elevating mechanism 3a is driven with the operation panel 17 to appropriately set the main body of elevating mechanism 3 in accordance with the size of patient and to adjust the height or tilting degree of the chin rest 11a by a chin rest positioning control circuit 11b. Then the radiography switch (not shown) is turned on with the operation panel 17, a rotation control motor 7a of the rotary table 7 and an X-axis control motor 8a and a Y-axis control motor 8b of the X-Y table 8 are controlled by a motor drive control circuit 20, and X-ray beam is horizontally rotated and horizontally moved in such a manner that the rotary arm 6 draws a predetermined envelope curve around the dental arch of the patient P. While the rotary arm 6 is operated, the X-ray tube 9a of the X-ray generator 9 is controlled by an X-ray control circuit 90, the X-ray beam is radiated to transmit through the first slit 12b, and is irradiated on the patient P. The X-ray through the second slit 16b is detected by the X-ray detection sensor 14b, thereby executing tomography of the entire jaw of dental arch. The rotary angle of rotary arm 6 is detected by an angle sensor 21.

The image signals output from the X-ray detection sensor 14b are output into a video memory 24, converted into digital signals by a signal processing means 22, then processed into a sectional image along an optional sectional plane by an image reconstruction means 23, and shown on an image display 26 like a cathode ray tube (called CRT for short), so that thus obtained images can be used for several diagnosis. The image reconstruction means 23 is specifically comprised of an image reconstruction program, and a central processing unit (CPU) 19 may be used for processing or other computer may be provided separately.

A work memory 27 necessary for signal processing is connected to the CPU 19 and further the operation panel 17 as an input means having a panel switch for selecting a radiography mode and an X-ray irradiation switch for controlling on/off of the X-ray irradiation is connected to the CPU 19. The CPU 19 is further connected with the motor drive control circuit 20, the first slit control circuit 12d, the second slit control circuit 16d, the X-ray control circuit 90 for controlling the X-ray generator 9, a control circuit 210 for up-and-down movement of an X-ray detection sensor for X-ray CT (MOS sensor) for controlling up-and-down movement of the imaging portion 300 comprised of the X-ray detection sensor for X-ray CT (MOS sensor) 14a, which is explained later, and a clock circuit 28 for outputting clock signals to synchronize the control operation of each control circuit 20, 12d, 16d, 90. The X-ray control circuit 90 can execute feedback control of the X-ray irradiation amount to the object (patient P) based on the signals imaged by the X-ray detection sensor 14b comprised of CCD. The control means 29 is constructed with the CPU 19, a frame memory 31, the work memory 27, the operation panel 17, the motor drive control circuit 20, the first slit control circuit 12d, the second slit control circuit-16d, the X-ray control circuit 90 and the clock circuit 28.

In case of executing X-ray CT, when a CT radiography mode is selected on the operation panel (input means) 17, the rectangular X-ray detection sensor 14a comprised of MOS on the X-ray detection sensor substrate 14 is positioned at the irradiation field of X-ray beam by driving the motor 15a, as mentioned hereinafter. Further, the rectangular slit 16a formed on the second slit board 16 is positioned in the front surface of the X-ray detection sensor 14a by driving the motor 16c. Then, which one of the X-ray detection sensors 14a or 14b is positioned is determined by the CPU 19 based on the output information of the determination circuit 18 for the kinds of X-ray detection sensor as mentioned above, and when the X-ray detection sensor 14a is positioned, whether it is the X-ray detection sensor provided for the imaging portion 300 which is movable up and down, as mentioned later is determined. When the positioned X-ray detection sensor 14a is the X-ray detection sensor provided for the imaging portion 300, the up and down position of imaging portion 300 is controlled with the control circuit 210 for up-and-down movement of X-ray detection sensor for X-ray CT (MOS sensor).

In the X-ray generator 9, the motor 13a is controlled to be driven by the first slit control circuit 12d to set the slit 12a for X-ray CT at an X-ray radiation port. The first slit control circuit 12d controls up and down position of the slit board 12 together with the support block 13 by driving the motor 13g2 relative to the up-and-down position of the imaging portion 300. The patient P is positioned with the operation panel 17 as mentioned above and a target region, a target tooth herein, is indicated on a display (not shown) on the operation panel 17, then the motor drive control circuit 20 is controlled to drive the X-axis control motor 8a and the Y-axis control motor 8b of the X-Y table 8, and the rotation center of the rotary arm 6 is positioned so as to meet the center of the target tooth. Such a positioning can be executed not only by horizontally moving the rotary arm 6 but also by horizontally moving a chair, which is provided on the base board 1 so as to be horizontally movable in a two-dimensional direction, while the patient is sitting on the chair. Further, the two-dimensional moving mechanism of the rotary means may be a two-dimensional moving mechanism using a polar coordinate instead of the X-Y table.

Thus the radiography switch (not shown) on the operation panel 17 is turned on, the arm rotation control motor 7a of the rotary table 7 is controlled with the motor drive control circuit 20 to rotate the rotary arm 6 around the rotation center which meets the center of the target tooth as mentioned above. While the rotary arm 6 is operated, the output of X-ray tube 9a of the X-ray generator 9 is controlled, X-ray beam is radiated via the first slit 12a into the target tooth of the patient P, and the X-ray transmitted through the second slit 16a is detected by the X-ray detection sensor 14a to be imaged. Such radiography is executed 360 degrees around the target tooth, and the obtained CT images are sequentially taken into the video memory 24. Radiography is executed 360 degrees, however, it is enough to execute radiography 180 degrees to construct CT images, so that radiography more than 180 degrees is adequate.

Figure 24:
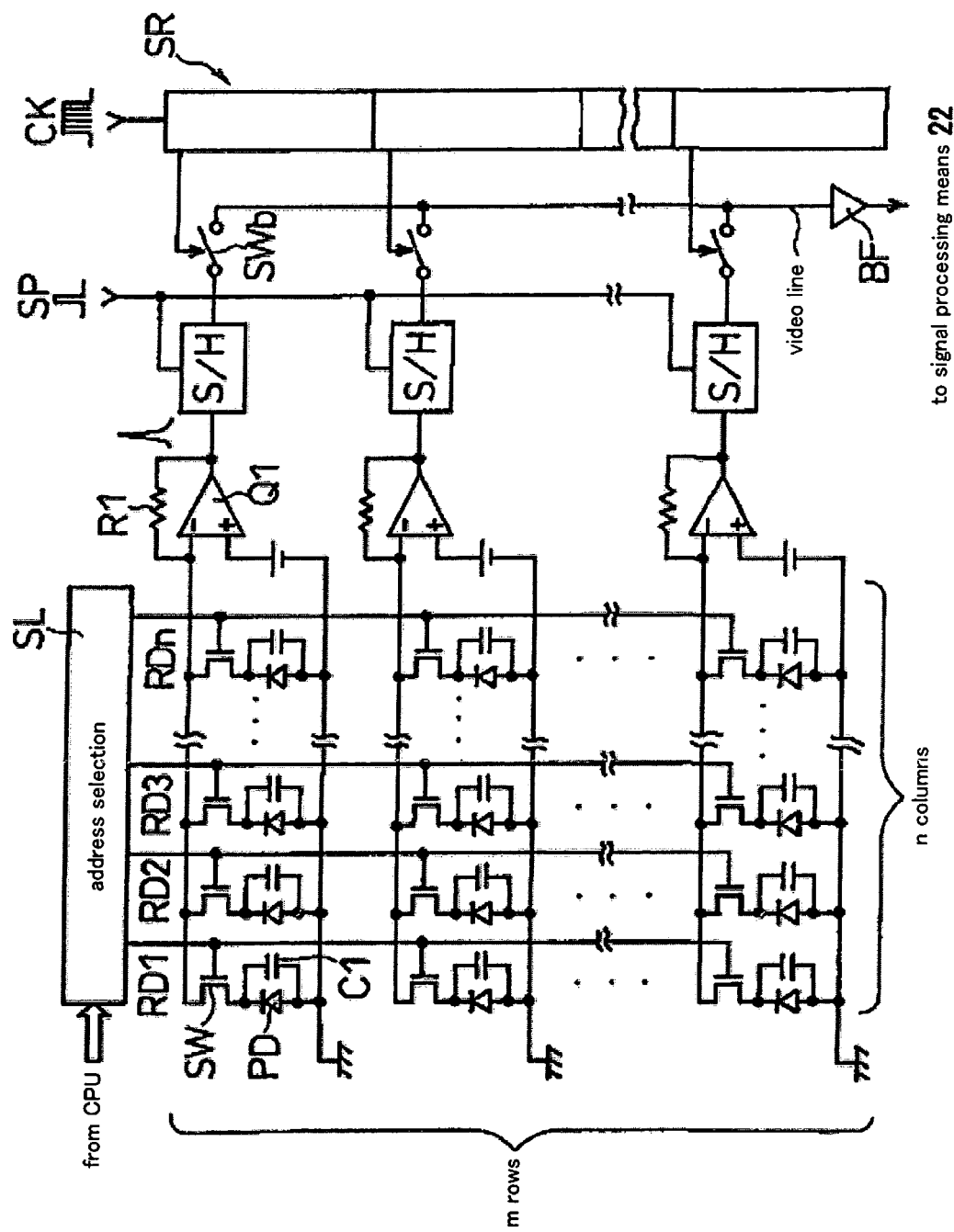
FIG. 24 is a driving circuit of an X-ray detection sensor comprised of MOS.

The X-ray detection sensor 14a comprised of MOS is designed such that plural photo diodes PD being light receiving elements are arranged in a matrix with m rows and n columns, a junction capacitance C1 is connected to each photo diode PD in parallel, and a read-out switch SW is connected thereto in series as shown in the drive control circuit in FIG. 24. Gate of switch SW is connected to an address selection circuit SL and the photo diode PD to be read out is selected based on the signals from the CPU 19. In this structure also panoramic radiography can be executed with the X-ray detection sensor 14a comprised of MOS. In this case, the slit 12b for panoramic radiography shown in FIG. 17 is used and the X-ray beam is made slit beam, thereby executing radiography. According to such structure, panoramic radiography is made possible with the X-ray detection sensor 14a comprised of MOS or with the elongated X-ray detection sensor 14b comprised of CCD and either radiography can be optionally selected.

The output side of switch SW is commonly connected in a unit of column to be input into an arithmetic amplifier Q1 constituting a current-voltage conversion circuit. The output of arithmetic amplifier Q1 is sampled at a sample hold circuit S/H. Each sample hold circuit S/H is connected to a switch SWb which is opened or closed by a shift register SR with m columns. Sequentially operating each open/close switch SWb, the sampled signals are transferred through a video line as time series signals to be output to a guide buffer BF. When such MOS is used, moving images can be obtained, so that the target position (sectional layer) can be optionally aimed by shifting the overlapped portions and accuracy of X-ray CT can be achieved. Further the X-ray detection sensor 14b may be comprised of MOS to execute panoramic radiography, so that the above-mentioned characteristic which is peculiar to MOS can be brought out when executing panoramic radiography.

Figure 7:
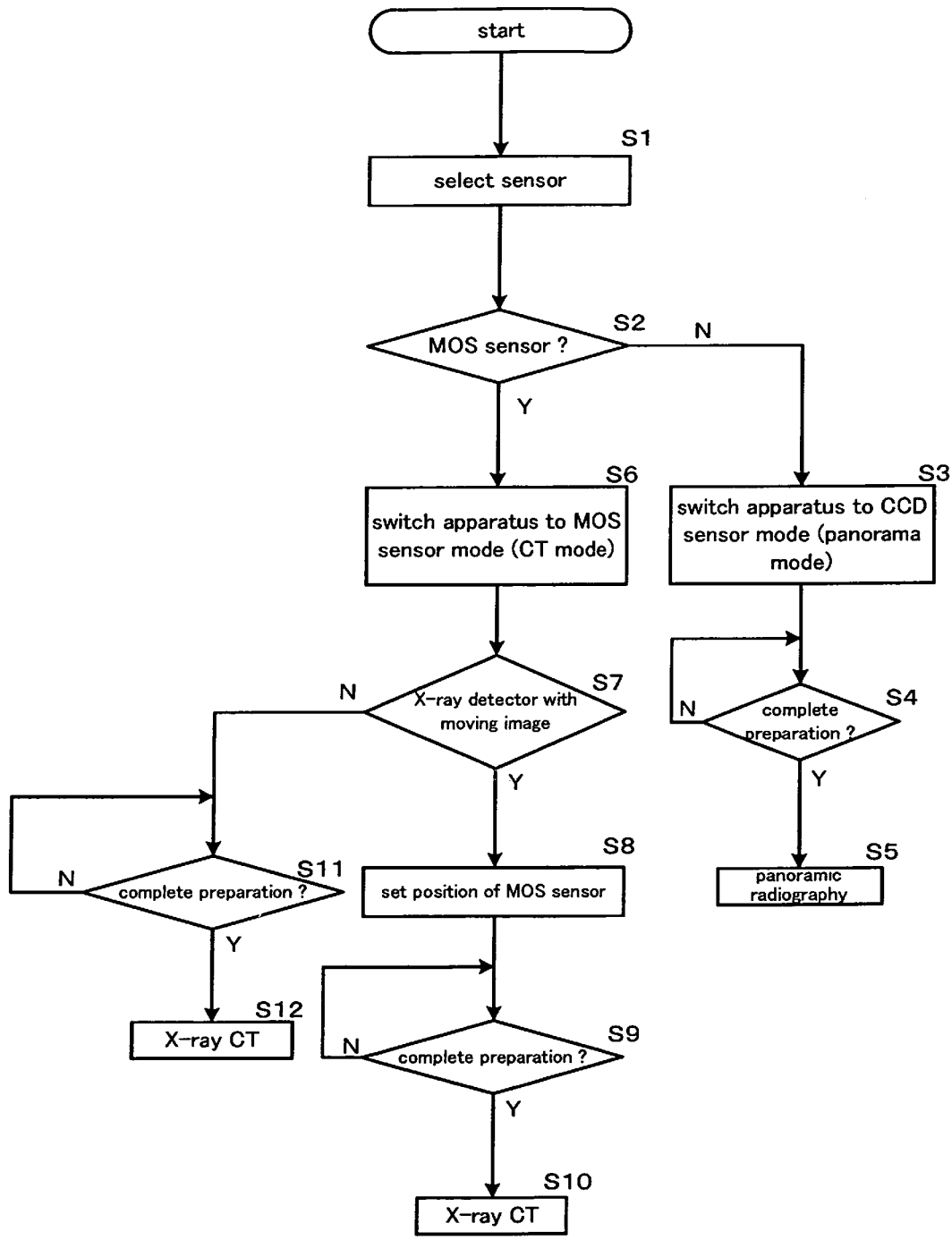
FIG. 7 is a flow chart showing basic operations of radiography mode according to the dental X-ray imaging apparatus.

FIG. 7 is a flow chart of radiography mode with the above-mentioned dental X-ray imaging apparatus in which one of the X-ray detection sensors 14a, 14b is selected and determined by the determination circuit 18 for the kinds of X-ray detection sensor at step S1, whether it is MOS sensor, namely the X-ray detection sensor 14a, or not is determined at step S2, if No, the apparatus is set at CCD sensor mode, namely panoramic radiography mode, at step S3. Completing preparation at step S4, panoramic radiography is executed. at step S5. If it is determined as MOS sensor at step S2, the apparatus is set at MOS sensor mode, namely X-ray CT mode at step S6. Whether the MOS sensor is the X-ray detection sensor provided for the imaging portion 300, as mentioned later, or not is determined at step S7, if YES, the up-and-down position of the imaging portion 300 is set at step S8, when preparation is completed at step S9, X-ray CT is executed at step S10. If NO at step S7, preparation is completed at step S11 and X-ray CT is executed at step S12.

Embodiment 2

Figure 8A:
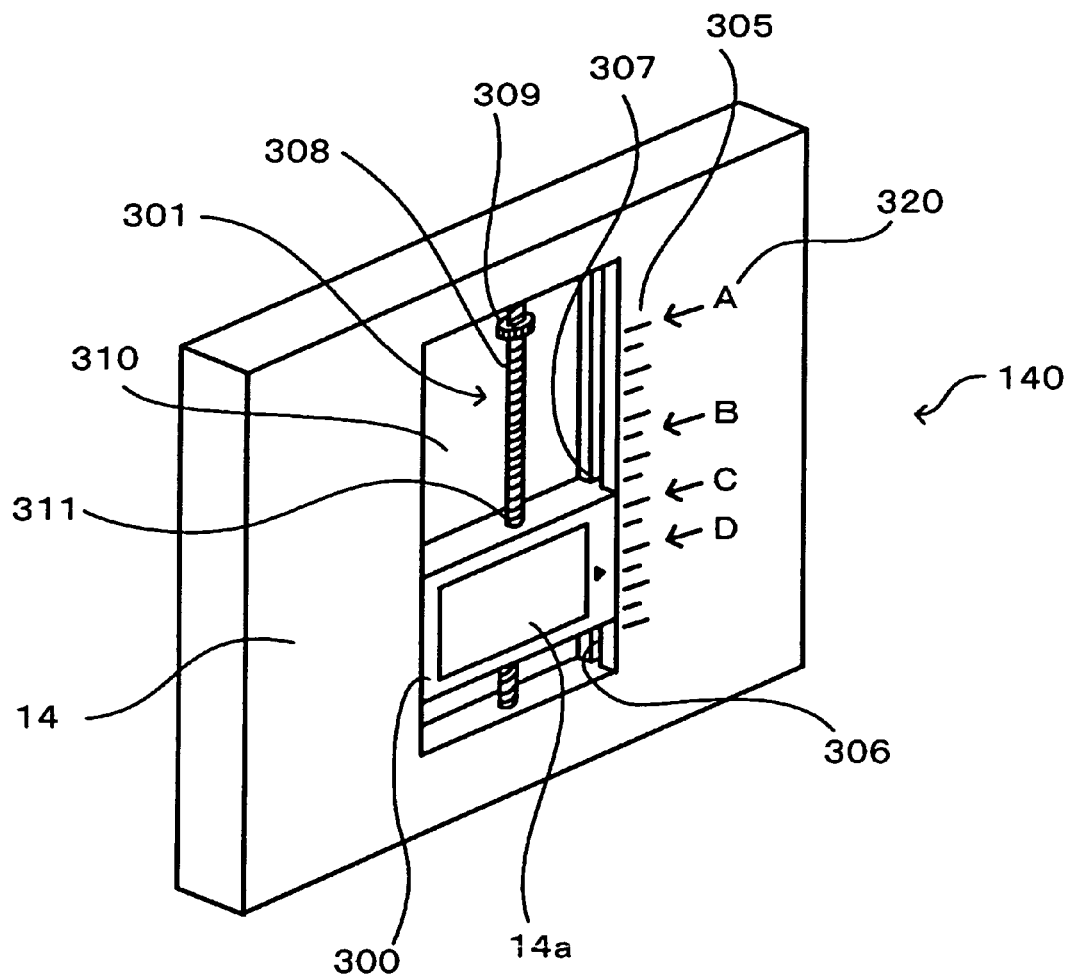
FIG. 8A shows a structure example of an X-ray detector applicable to the present invention.

FIG. 8A shows an preferable embodiment of the X-ray detector 140 attached to the X-ray detecting portion 10. The X-ray detector 140 is comprised of the substrate 14 formed as a cassette detachable to the sensor holder 15, the X-ray detection sensor (electric imaging means) 14a comprised of plane MOS extending into a two-dimensional direction, the imaging portion 300 comprised of the X-ray detection sensor 14a and an imaging portion positioning means 301 for moving up and down the imaging portion 300 in the substrate 14.

A projection 307 is provided at both sides of the imaging portion 300. A rectangular opening 310 is provided at the center of the substrate 14 and the imaging portion 300 is formed in such size and shape as to be moved up and down in the opening 310. A concave groove 306 is provided for the opening 310 corresponding to the projection 307 such that the projection 307 is fitted in the groove 306.

Hole 311 of which inside is screwed is penetrated through the imaging portion 300. A ball screw 308 with a screw shaft extending vertically is provided at the center of the opening 310 and a ring 309 which is manually screwed is provided for the ball screw 308 and passes through the hole 311.

The ball screw 308 is screwed by manually operating the ring 309, the projection 307 is guided in the concave groove 306, then the imaging portion 300 moves up and down in the opening 310. When seen entirely, the imaging portion 300 is vertically positioned in the X-ray detector 140.

The shifted amount is preferably shown by adding a graded scale 305 at either left or right of the opening 310 or both sides thereof.

More preferably, an index 320 is provided for important regions to be an objective imaging region at either left or right of the opening 310 or both sides thereof.

In the embodiment of FIG. 8A, the index arrow "A" shows stapes as an important objective imaging region in otolaryngology, "B" shows a temporomandibular joint as an important objective imaging region in dentistry and "C" shows an upper jaw, and "D" shows a lower jaw. Illustrations of stapes, a temporomandibular joint, an upper jaw and a lower jaw which are commonly used in the world may be used instead of these alphabets.

Figure 8B:
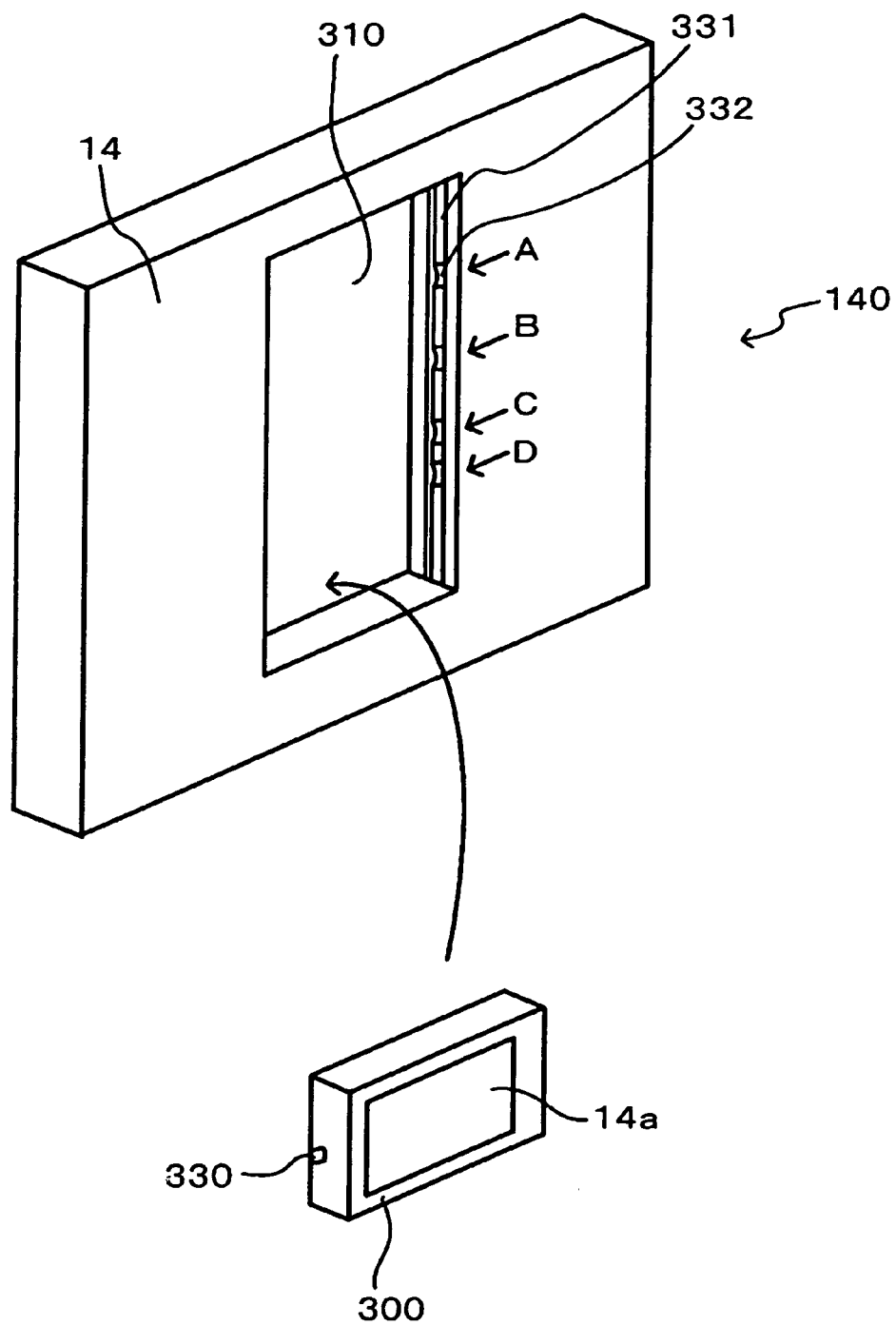
FIG. 8B shows other structure example of an X-ray detector applicable to the present invention.

The structure for manually moving the imaging portion 300 may be varied other than the embodiment of FIG. 8A, and one of examples is shown in FIG. 8B.

Energized projection 330 is provided at left and right sides of the imaging portion 300. The imaging portion 300 is designed to shift up and down in the opening 310 and a concave groove 331 is provided at the position corresponding to the projection 330. A deep groove hole 332 is provided at plural portions of the concave groove 331.

Figure 8C:
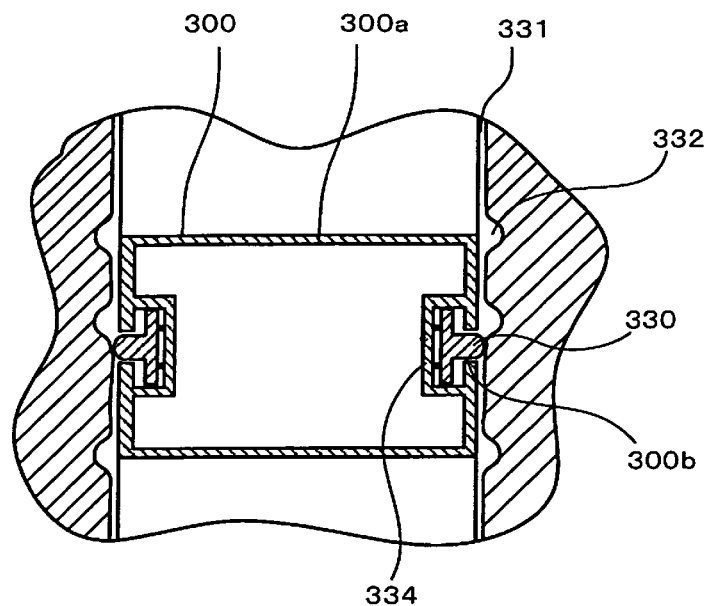
FIG. 8C is an explanatory view of a partial section of FIG. 8B.
Figure 8C:
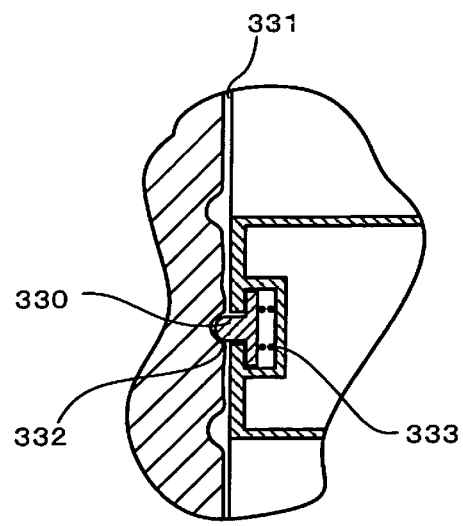

FIG. 8C shows the projection 330 is fitted in the concave groove 331. The projection 330 is energized to outside of a casing 300a with a spring 333 contacting with a wall 334 provided in the casing 300a of the imaging portion 300 and one part thereof is projected out of an opening 300b provided at right and left sides of the casing 300a. The projection 330 is larger than the opening 300b, so that the portions other than the projected part are stopped with the opening 300b and are not projected further. The structure in the casing 300a is omitted.

The projection 330 is slid in the concave groove 331 and is pushed back into the inside of the casing 300a in force at the position other than the groove hole 332 by regulated with the bottom of the concave groove 331 shallower than the groove hole 332.

In the embodiment shown in FIG. 8B, the groove hole 332 is stepwisely provided for the portion corresponding to the arrows "A"-"D" shown in FIG. 8A.

Plural groove holes 332 may be provided at small intervals so as to stop at a desired position. Operator manipulates the imaging portion 300 up and down and the projection 330, the concave groove 331, the groove hole 332 and the spring 333 do not apply outer force on the imaging portion 300 to be moved up and down, however they function as the imaging portion positioning means to guide or position the imaging portion 300.

FIG. 9A-FIG. 9D show modified embodiments of the X-ray detector 140 attached to the X-ray detecting portion 10. The basic structure of FIG. 9A-FIG. 9D is the same as that of FIG. 8A, so the basic structure is not explained here.

Figure 9A:
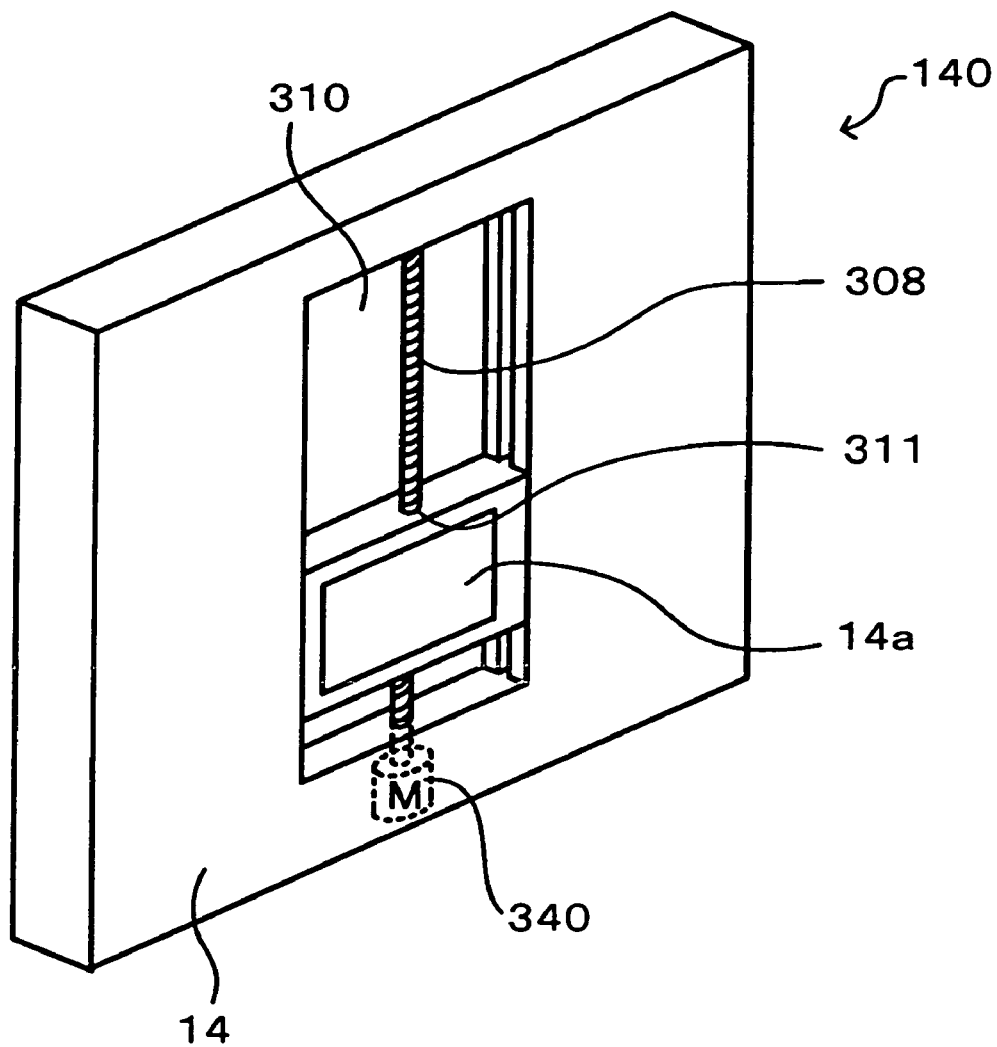
FIG. 9A shows an modified embodiment of an X-ray detector.

FIG. 9A is constructed similar to FIG. 8A, however they are different in that the screw shaft 308 is operated with a motor 340 automatically, not manually.

In FIG. 9A, the imaging portion 300 may be controlled so as to automatically and stepwisely move up and down corresponding to the important objective imaging regions like the above-mentioned stapes, a temporomandibular joint, an upper jaw and a lower jaw of the object to be examined.

Figure 9B:
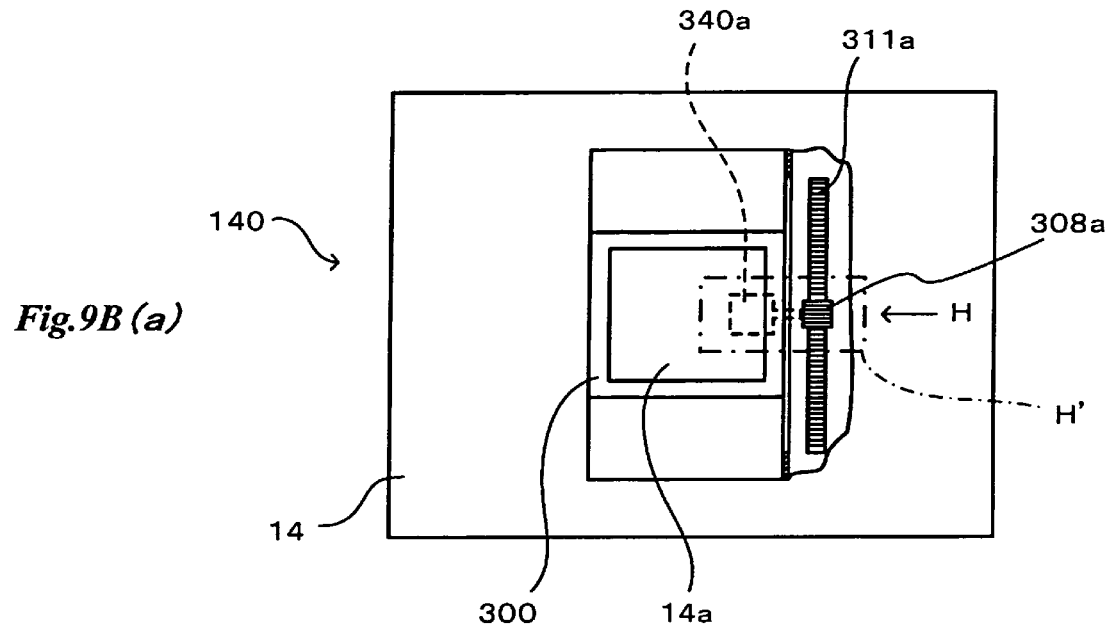
FIG. 9B shows other modified embodiment of an X-ray detector.
Figure 9B:
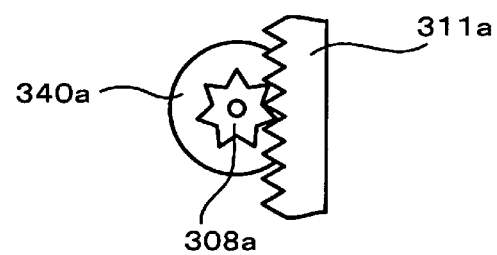

In FIG. 9B, a gear 308a, a rack 311a and a motor 340a are provided instead of the screw shaft 308, the hole 311 and the motor 340 which are used in FIG. 9A. The rack 311a extending in a vertical direction is provided for the substrate 14, the motor 340a is fixed into the imaging portion 300, and the gear 308a is inserted into the driving shaft of the motor 340a, thereby the gear 308a is engaged with the rack 311a. The gear 308a is driven and rotated by driving the motor 340a to shift the imaging portion 300 up and down.

FIG. 9B(b) shows the motor 340a, the gear 308a, and the rack 311a within the area H' shown with dotted line, which is seen from the direction indicated with the arrow H.

Figure 9C:
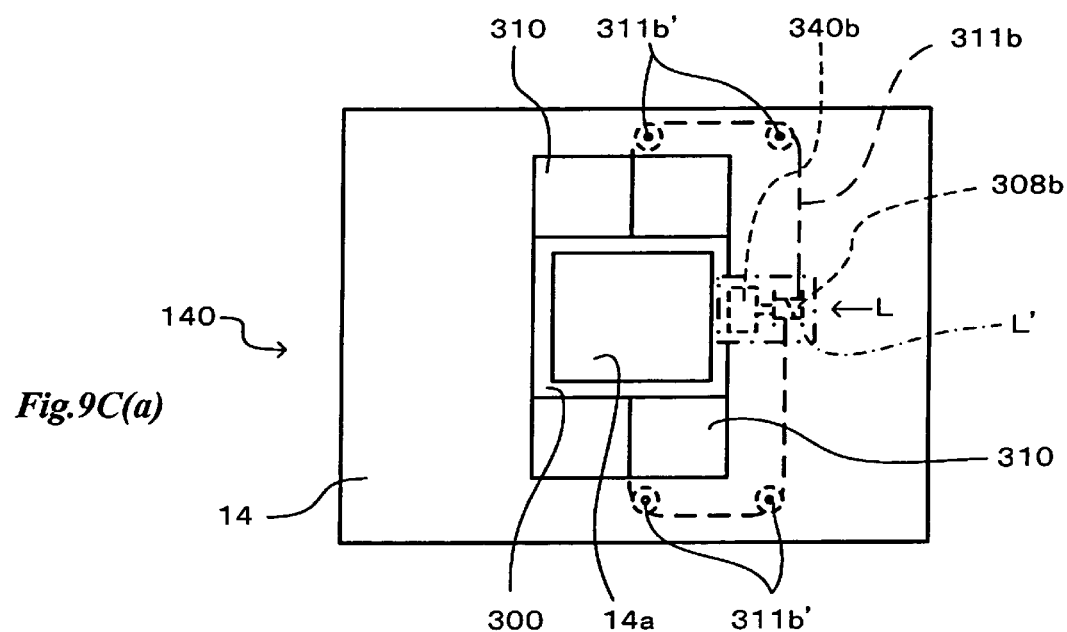
FIG. 9C shows still other modified embodiment of an X-ray detector.
Figure 9C:
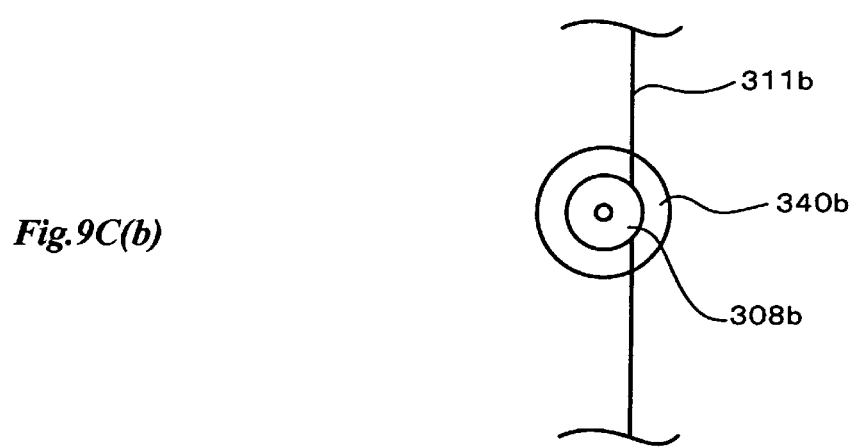

In FIG. 9C, a driving pulley 308b, a belt 311b, and a motor 340b are provided instead of the screw shaft 308, the hole 311 and the motor 340 which are used in FIG. 9A. The motor 340b is fixed at the center of the right side of the substrate 14 and the driving pulley 308b is inserted into the driving shaft of the motor 340b. The belt 311b is engaged with the driving pulley 308b to be guided with plural guide pulleys 311b' fixed in the substrate 14 so that each edge is inwardly exposed from the upper edge and the lower edge of the opening 310 provided for the substrate 14 to be fixed at the upper edge and the lower edge of the imaging portion 300 respectively. The driving pulley 308b is driven and rotated by driving the motor 340b to drive the belt 311b, thereby the imaging portion 300 is shifted up and down.

FIG. 9C(b) shows the motor 340b, the driving pulley 308b, and the belt 311b within the area L' shown with dotted line, which is seen from the direction indicated with the arrow L.

Figure 9D:
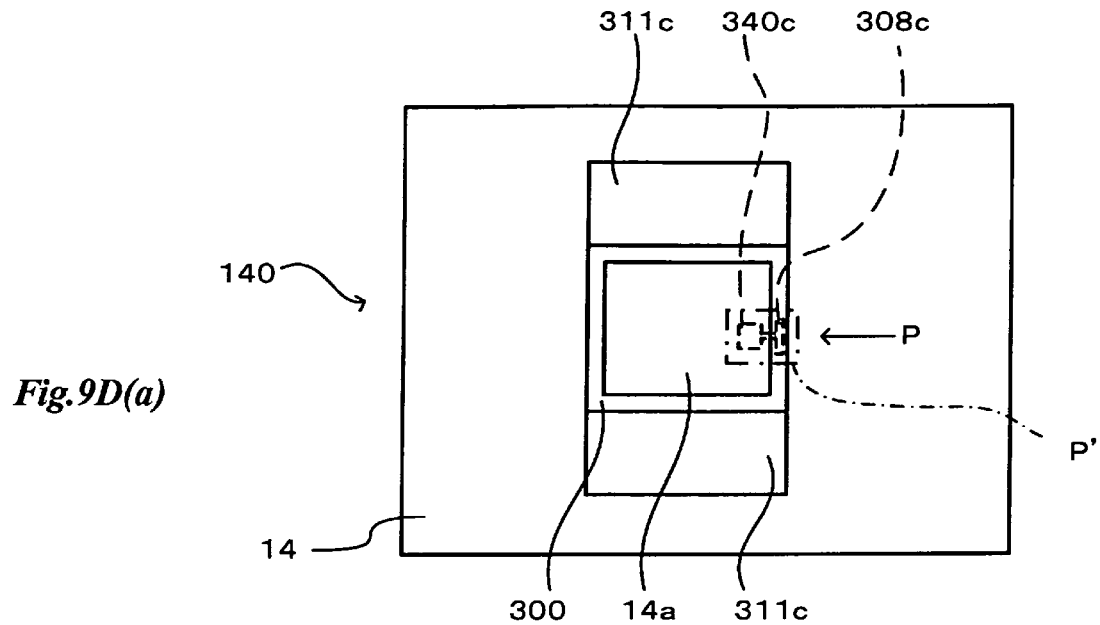
FIG. 9D also shows still other modified embodiment of an X-ray detector.
Figure 9D:
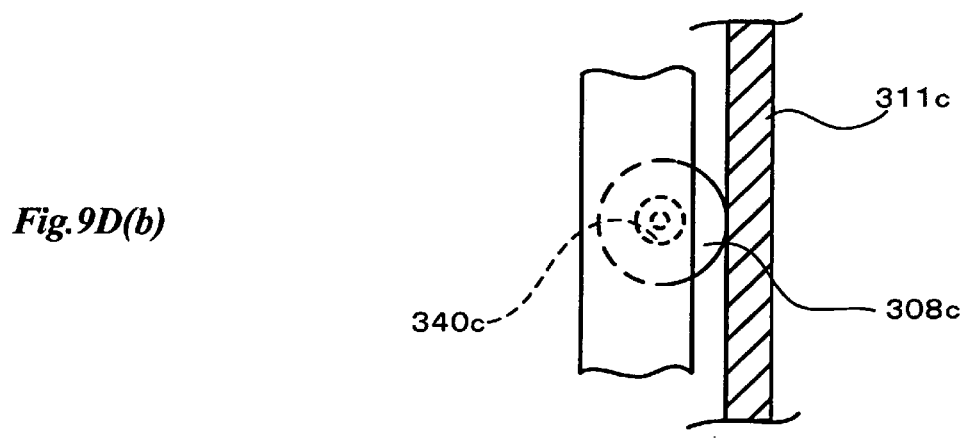

In FIG. 9D, a roller 308c, a back plate 311c, and a motor 340c are provided instead of the screw shaft 308, the hole 311 and the motor 340 which are used in FIG. 9A. The back plate 311c is provided for the entire back surface of the substrate 14, at least the portion corresponding to the opening 310 provided for the substrate 14, the motor 340c is fixed on the imaging portion 300, and the roller 308c is inserted in the driving shaft of the motor 340c, the roller 308c contacting with the back plate 311c. The roller 308c is driven to be rotated by driving the motor 340c and the roller 308c itself is shifted relative to the back plate 311c by friction, thereby shifting the imaging portion 300 up and down.

FIG. 9D(b) shows the motor 340b, the roller 308c, and the back plate 311c within the area P' shown with dotted line, which is seen from the direction indicated with an arrow P.

Figure 18:
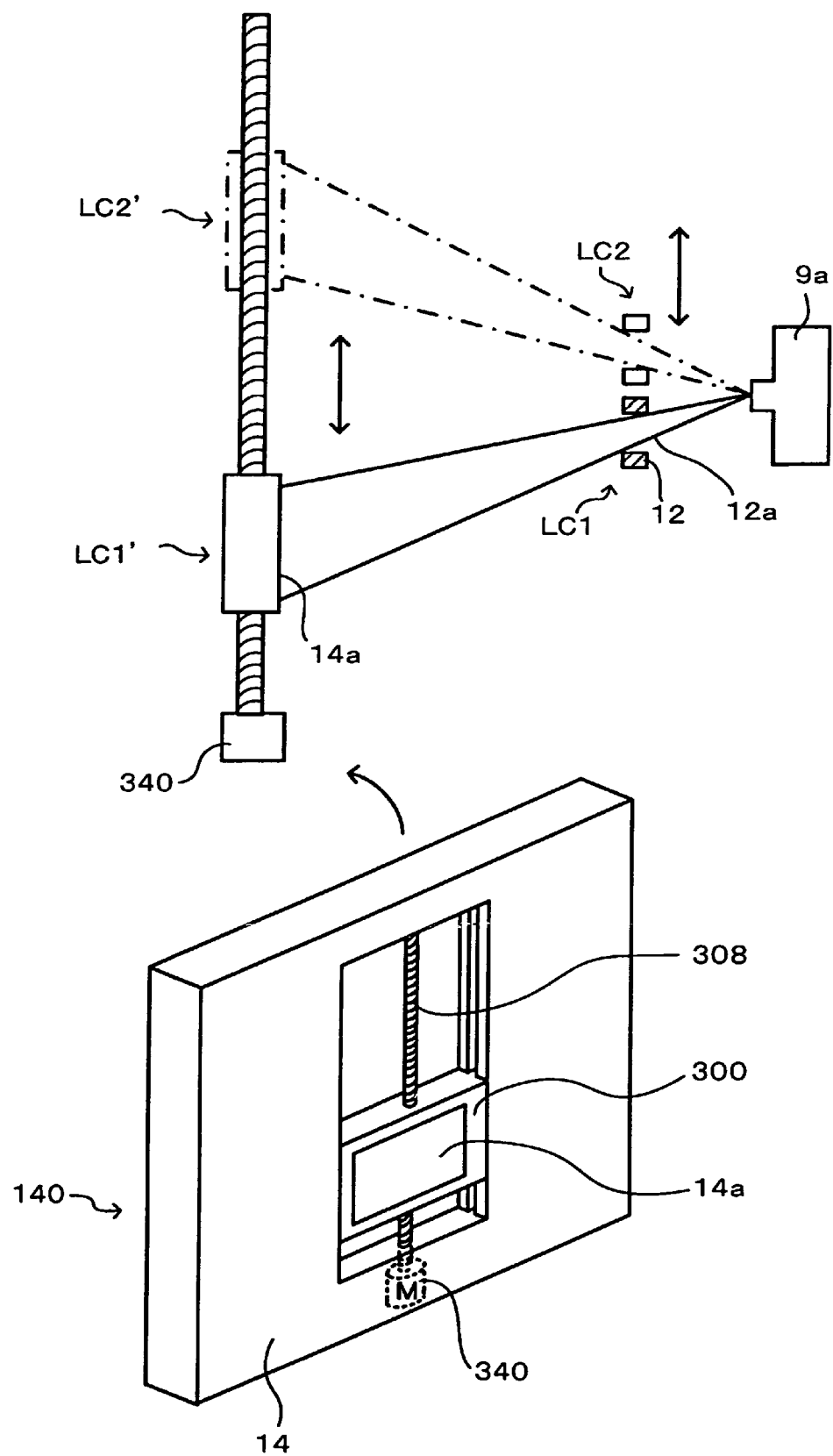
FIG. 18 shows one example of an elevating and shifting mechanism of an imaging portion.

FIG. 18 shows a diagrammatical explanatory view for changing the irradiating direction of X-ray beam by moving the first slit board 12 shown in FIG. 17 up and down corresponding to the up-and-down movement of the imaging portion 300 of the X-ray detector 140 shown in FIG. 8 and FIG. 9.

The X-ray beam generated from the X-ray tube 9a is irradiated through the slit 12a for X-ray CT of the first slit board 12 at a position LC1 into the X-ray detection sensor 14a of the imaging portion 300 at a position LC1'.

When the imaging portion 300 is moved up at a position LC2', the first slit board 12 is also moved up and X-ray beam is irradiated from the slit 12a for X-ray CT at a position LC2 into the X-ray detection sensor 14a of the imaging portion 300 at a position LC2'. In this case, the elevating mechanism of the first slit board 12 functions as an irradiating direction changing means for changing the irradiating direction of X-ray beam.

Either one of positioning of the imaging portion 300 and positioning of the first slit board 12 may be executed at first or they may be executed simultaneously.

FIG. 18 shows an embodiment for shifting the imaging portion 300 up and down in which the elevating mechanism of the first slit board 12 shown in FIG. 17 is applied and X-ray CT can be executed corresponding to the imaging region using a large sheet of sensor without moving the imaging portion up and down.

Figure 19:
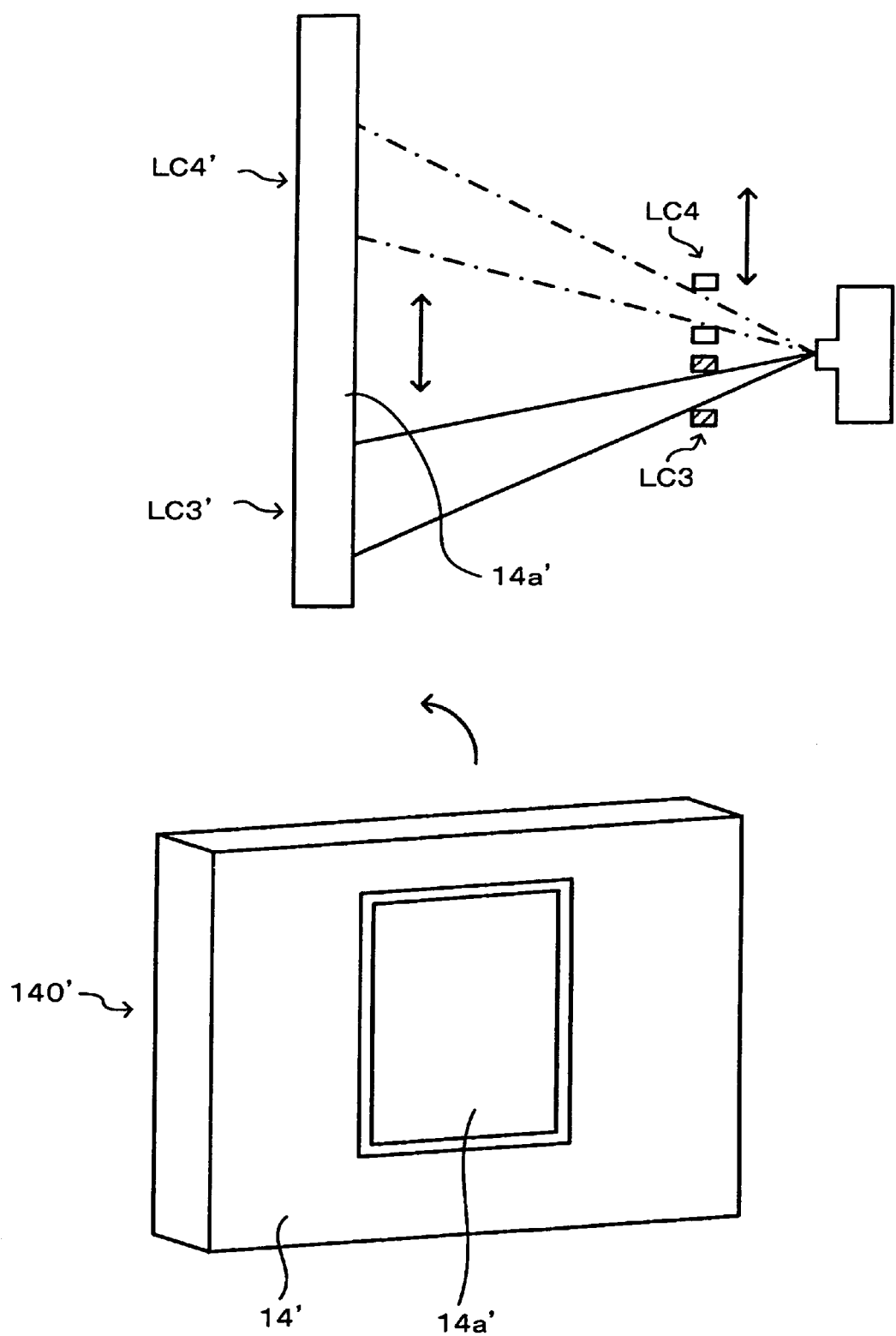
FIG. 19 is a diagrammatic explanatory view of X-ray CT.

FIG. 19 is a diagrammatical explanatory view showing an example thereof.

An X-ray detector 140' in FIG. 19 has a large sheet of X-ray detection sensor 14a' being a wide two-dimensional electric imaging means with such a detection area enough to capable of entirely detecting the area, without moving, the area being detected by moving the X-ray detection sensor 14a in FIG. 18 up and down. The X-ray detection sensor 14a' is a plane electric imaging means extending into a two-dimensional direction which is used for X-ray CT and constitutes an imaging portion of the X-ray detector 140'.

The X-ray beam generated from the X-ray tube 9a is irradiated into the irradiation field at a position LC3' on the X-ray detection sensor 14a' through the slit 12a for X-ray CT on the first slit board 12 at a position LC3.

The X-ray beam can be shifted so as to be irradiated on the irradiation field at a position LC4' on the X-ray detection sensor 14a' through the slit 12a for X-ray CT at a position LC4 by moving the first slit board 12 up and down.

In this case, the elevating mechanism of the first slit board 12 functions as an irradiation field changing means for changing placement of the irradiation field of X-ray beam up and down.

Means for changing the irradiating direction according to the position of the imaging portion which moves up and down is called as the irradiating direction changing means and means for changing the position of irradiation field within the area of the imaging plane of the imaging portion is called as the irradiation field changing means, however, the similarly constructed means can be used as mentioned above.

FIG. 18 explains an embodiment in which the irradiating direction of X-ray beam is varied by shifting the first slit board 12 and FIG. 19 explains an embodiment in which the position of irradiation field of X-ray beam is varied by shifting the first slit board 12, however, there are other structures to change the irradiating direction of X-ray beam and the position of irradiation field of X-ray beam.

Figure 20A:
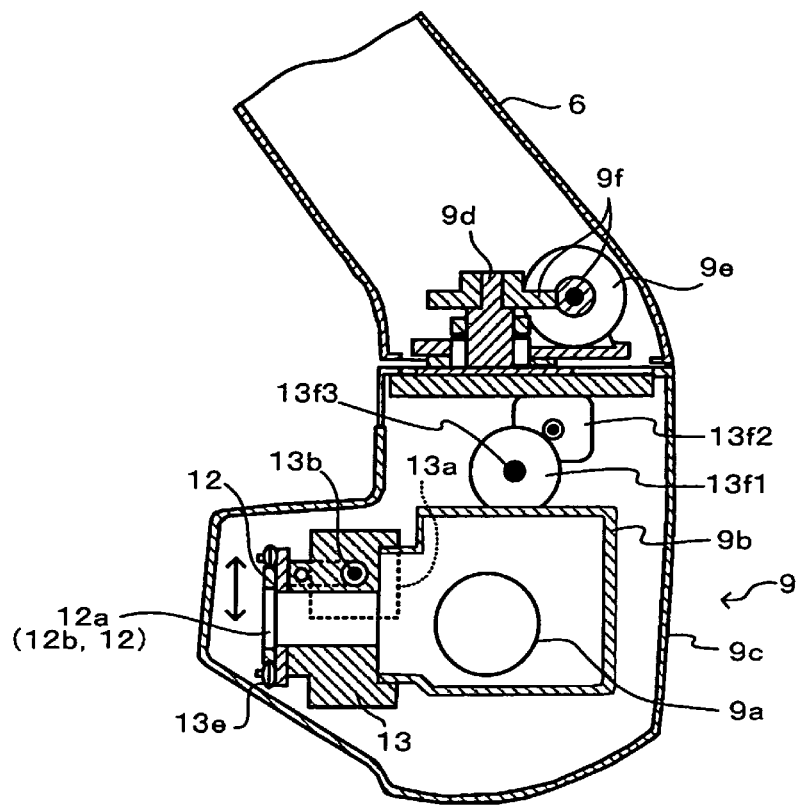
FIG. 20(a) and FIG. 20(b) show a mechanism for shifting the angle of X-ray tube.
Figure 20B:
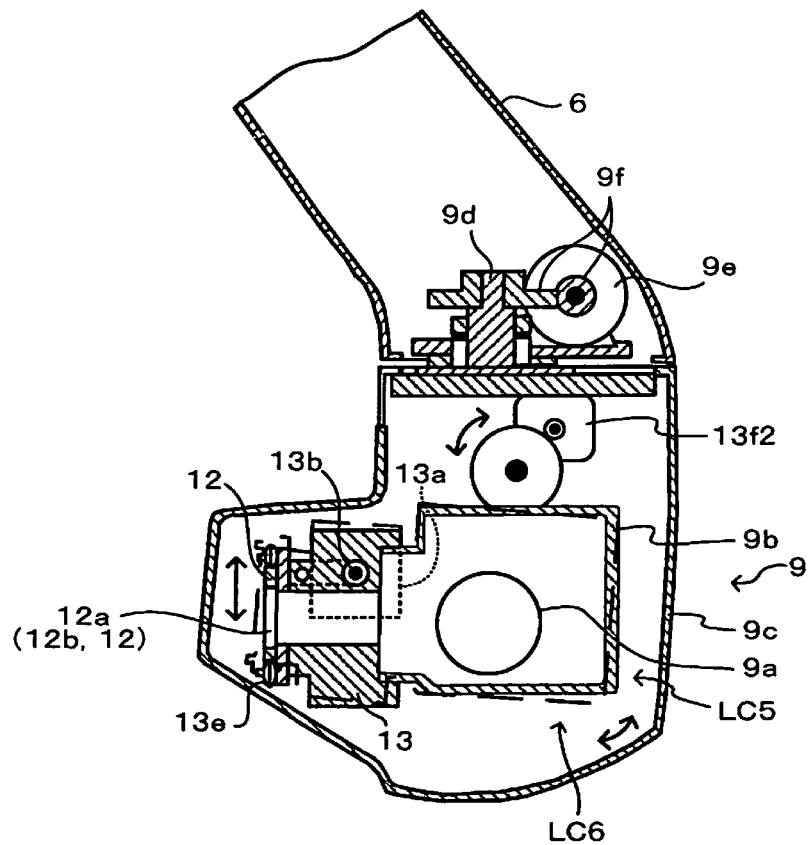
Figure 21:
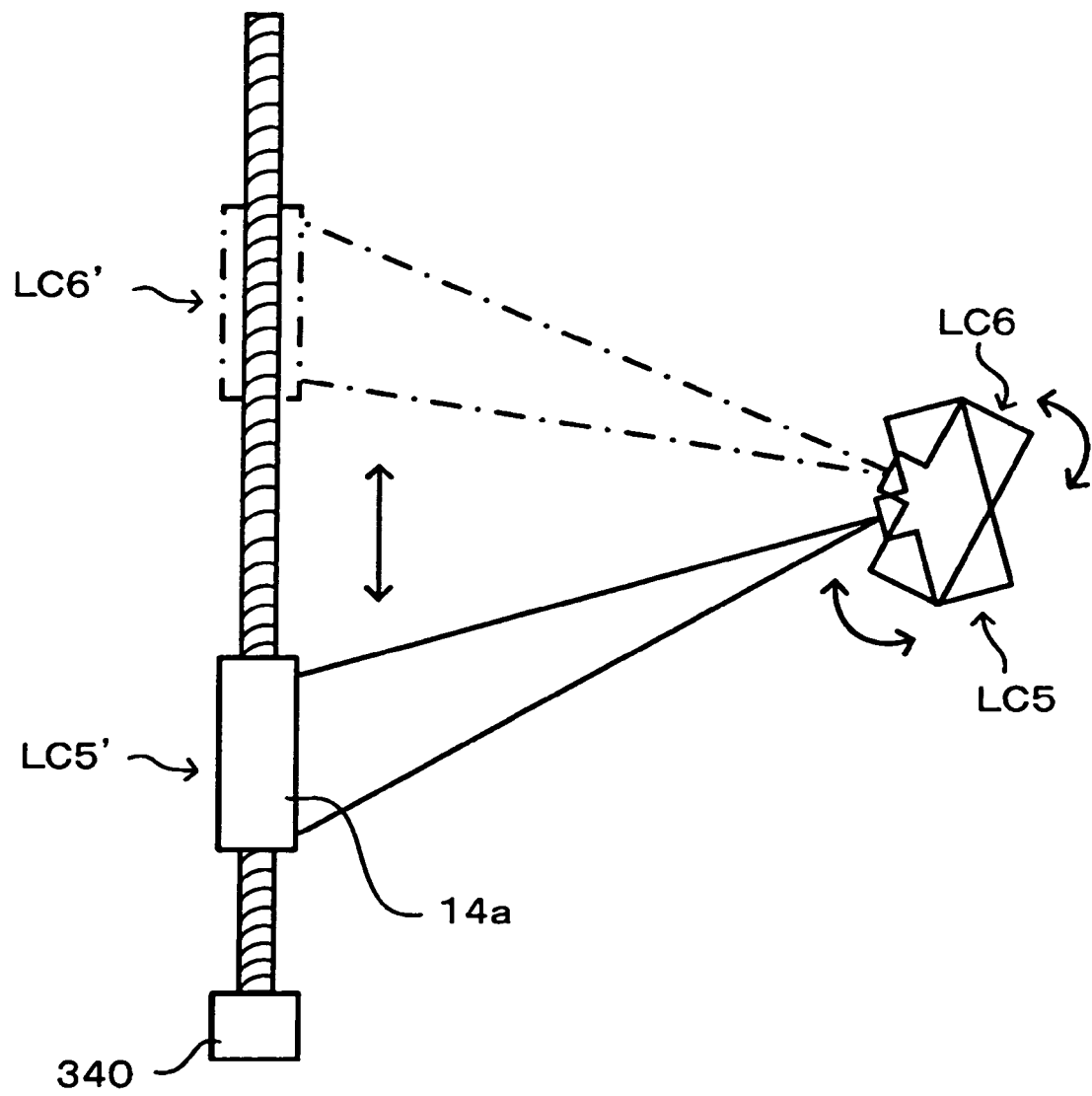
FIG. 21 shows other embodiment of an elevating and shifting mechanism of an imaging portion.
Figure 22:
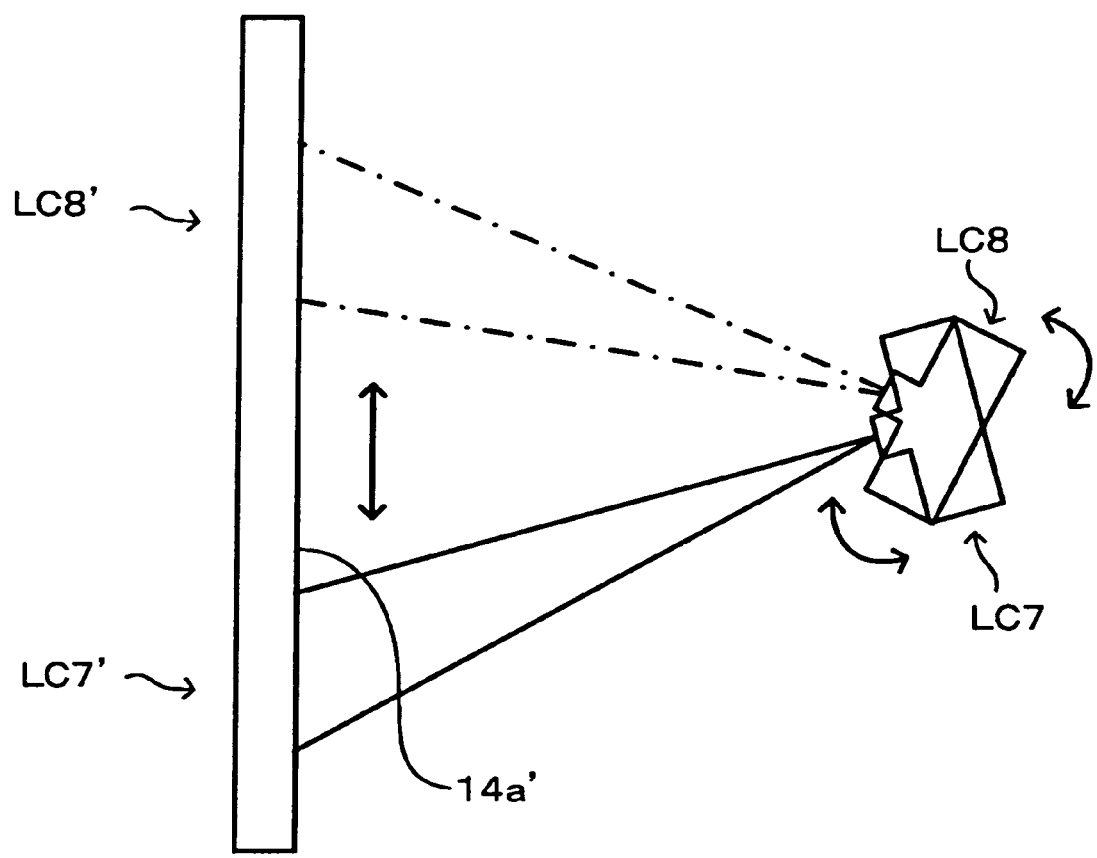
FIG. 22 is a diagrammatic explanatory view of an embodiment having a large sheet of X-ray detection sensor.

FIG. 21 and FIG. 22 show an embodiment in which the X-ray generator itself is tilted and the X-ray generator shown in FIG. 20 is used.

FIG. 20 is different from FIG. 17 in that there is no mechanism for moving the first slit board 12 up and down and the inner case 9b incorporating the X-ray tube 9a is subjected to angular shift. A gear 13f1 is fixed into the inner case 9b in such a manner that the inner case 9b is rotatably and axially supported with a horizontal shaft 13f3. The inner case 9b is entirely rotated by driving the gear 13f1 with a motor 13f2. The reference numeral LC5 indicates a position before rotation and LC6 indicates a position after rotation.

FIG. 21 is a diagrammatical explanatory view in which the imaging portion 300 is moved up and down like FIG. 18.

FIG. 21 has the same structure as FIG. 18 except that the first slit board 12 does not move up and down and the X-ray tube 9a is rotated, therefore it is briefly explained here.

X-ray beam is irradiated into the X-ray detection sensor 14a of the imaging portion 300 at a position LC5' from the X-ray tube 9a at a position LC5, and is further irradiated into the X-ray detection sensor 14a of the imaging portion 300 at a position LC6' from the X-ray tube 9a at a position LC6.

FIG. 22 is a diagrammatical explanatory view of an embodiment having a large sheet of X-ray detection sensor 14a' like FIG. 19.

FIG. 22 has the same structure as FIG. 19 except that the first slit board 12 does not move up and down and the X-ray tube 9a is rotated, therefore it is briefly explained here.

X-ray beam is irradiated into the irradiation field at a position LC7' on the X-ray detection sensor 14a' from the X-ray tube 9a at a position LC7, and is further irradiated into the irradiation field at a position LC8' from the X-ray tube 9a at a position LC8.

Figure 10:
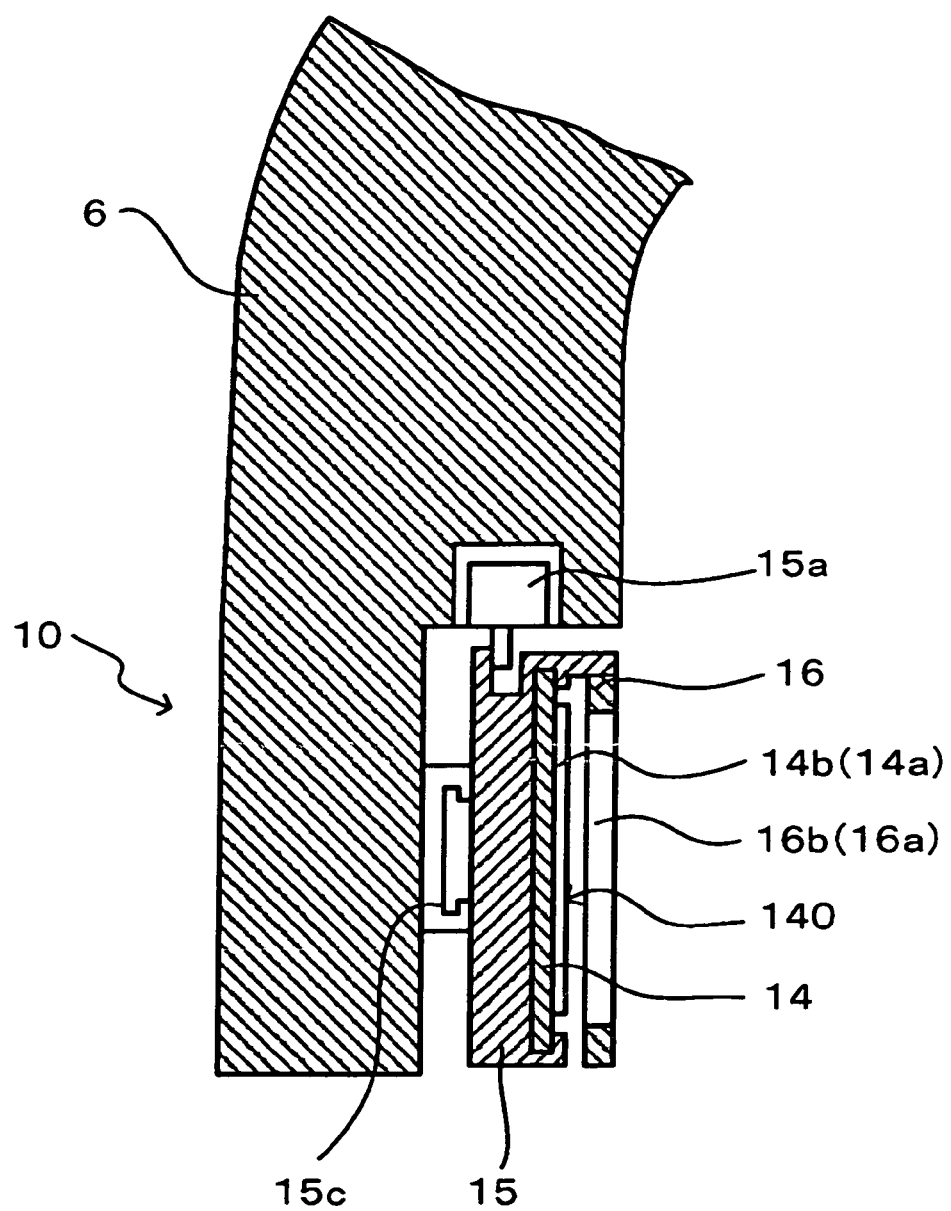
FIG. 10 is a vertical sectional view showing one embodiment of an electric imaging means attached to an X-ray detecting portion.
Figure 11:
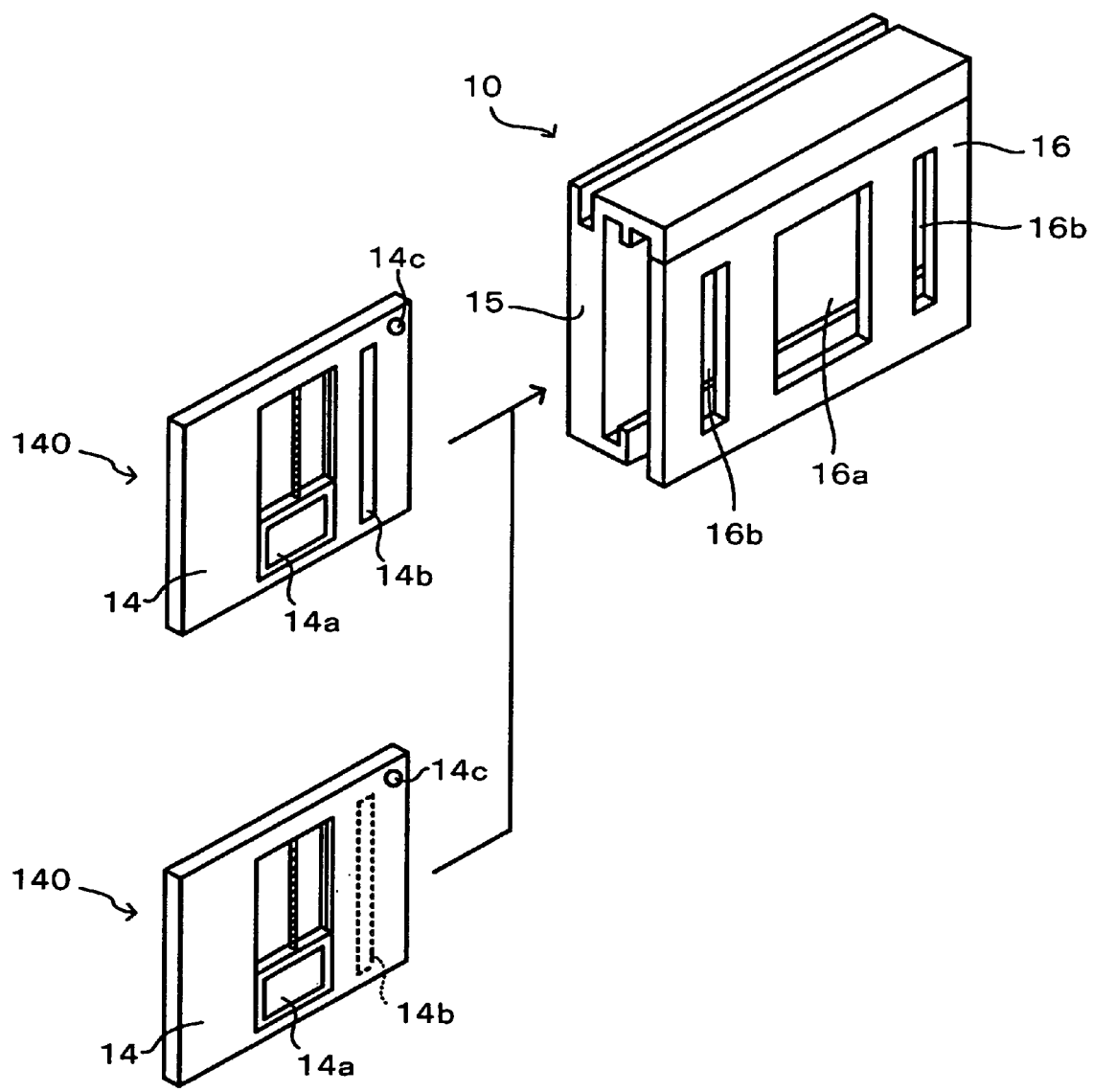
FIG. 11 is an exploded perspective view of the essential part of the X-ray detecting portion.

FIG. 10 and FIG. 11 show another embodiment of an electric imaging means, namely an X-ray detector, attached to the X-ray detecting portion 10 in which the X-ray detection sensor substrate 14, namely the X-ray detector 140, formed with two kinds of X-ray detection sensors 14a, 14b is detachably attached to the sensor holder 15 integrated with the second slit board 16. The X-ray detection sensor 14a is a plane electric imaging means extending into a two-dimensional direction and is comprised of a rectangular MOS (about 120 mm×120 mm). The X-ray detection sensor 14b is an elongated electric imaging means and is comprised of an elongated CCD (about 150 mm×6 mm). However, both of them may be comprised of MOS. The X-ray detection sensor 14a is constructed such that the imaging portion moves up and down as shown in FIG. 8 and FIG. 9. The sensor holder 15 is supported at the end of the rotary arm 6 via a slide mechanism 15c made of a guide body and a slide member so as to be slidable right and left and is capable of lateral movement (shift) with a motor 15a. Two kinds of second slits 16a, 16b are provided for the second slit board 16 and they correspond to the X-ray detection sensors 14a, 14b respectively as mentioned above. Any one of the X-ray generator 140 shown in the upper part of FIG. 11 and the X-ray generator 140 shown in the lower part of FIG. 11 may be used.

An output connector (not shown) is provided for the X-ray detection sensor substrate 14 corresponding to the X-ray detection sensors 14a, 14b and is designed to be connected to an input provided for the X-ray detecting portion 10 when being connected to the X-ray detecting portion 10 via the sensor holder 15 as mentioned above. The upper X-ray detector 140 in FIG. 11 is constructed such that two kinds of X-ray detection sensors 14a, 14b are provided at one surface of the X-ray detection sensor substrate 14 and the lower X-ray detector 140 in FIG. 11 is designed such that the two kinds of X-ray detection sensors 14a, 14b are provided for both surfaces of the X-ray detection sensor substrate 14 respectively. (The X-ray detection sensor 14b shown with dotted line is provided at the rear face.) In the latter case, the X-ray detector 140 is reversed to be attached according to a desired radiography mode. In order to discriminate the surfaces, an identifier 14c such as an IC chip is attached on the surface of the X-ray detection sensor substrate 14, by which the surface is discriminated by a detection means (not shown) provided in the sensor holder 15 when the X-ray detector 140 is attached to the sensor holder 15. The identifier 14c also provides information whether the X-ray detector 140 is an X-ray detector for moving the imaging portion 300 up and down or not.

Figure 12:
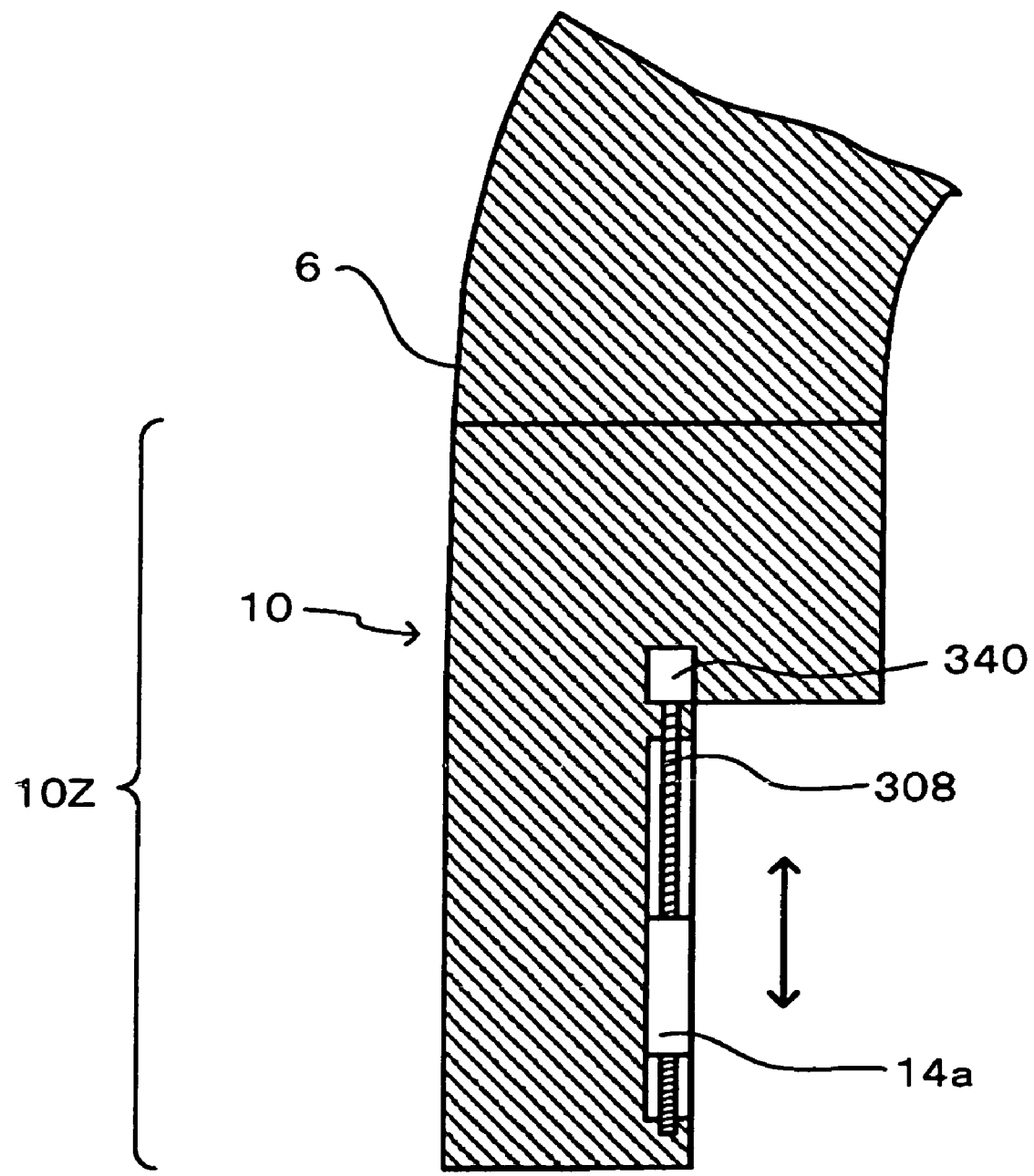
FIG. 12 is a vertical sectional view showing other embodiment of an X-ray detecting portion.

Such an X-ray detector 140 is detachable to the sensor holder 15, thereby facilitating maintenance in case of repairing and exchanging. If the X-ray detection sensor 14b is made long about 225 mm×6 mm, it can be used also for cephalometric radiography when it is attached to the X-ray detecting portion 5d for cephalometric radiography unit 5. The embodiments for executing panoramic radiography and X-ray CT using the X-ray detector 140 are the same as mentioned above, so they are not explained here. The above explanation shows a structure such that the X-ray detector 140 is detachable to the X-ray detecting portion 10, however, the X-ray detector 140 may be fixed, not detachable. The X-ray detector 140 may be fixed on the sensor holder 15 of the X-ray detecting portion 10 so as to be slid (shifted) as explained referring to FIG. 10 and FIG. 11. Otherwise, the X-ray detector 140 and the X-ray detecting portion 10 are not required to be separate, and they may be integrally formed as shown with the reference numeral 10z in FIG. 12. The reference numeral 10z in FIG. 12 is a unit at the X-ray detecting portion and is not detachable to the rotary arm 6, however, it may be removed with tools. The X-ray detecting portion of an existing panoramic radiography apparatus may be removed to be exchanged with the unit 10z at the X-ray detecting portion of the present invention. Further the X-ray detecting portion of an existing panoramic radiography apparatus may be removed to be exchanged with the unit at the X-ray detecting portion having the X-ray detecting portion as shown in FIG. 10 and FIG. 11. In this case, in addition to the unit at the X-ray detecting portion, a control means for X-ray irradiation timing, the irradiation field of X-ray beam and the rotary means, the first slit, and an image reconstruction means required for X-ray CT may be constructed as the X-ray CT unit for adding a CT radiography function of the present invention to the existing panoramic X-ray imaging apparatus.

The "elongated" shape of the X-ray detection sensor 14*b* which is an elongated electric imaging means and the "plane shape extending in a two-dimensional direction" of the X-ray detection sensor 14*a* which is a plane electric imaging means extending in a two-dimensional direction referred in the present application are explained hereinafter as a preferred example.

The reference numeral Sf1 indicates a detection surface of the X-ray detection sensor 14*b* which is an elongated electric imaging means and the reference numeral Sf2 indicates a detection surface of the X-ray detection sensor 14*a* which is a plane electric imaging means extending in two-dimensional direction.

Figure 25A:
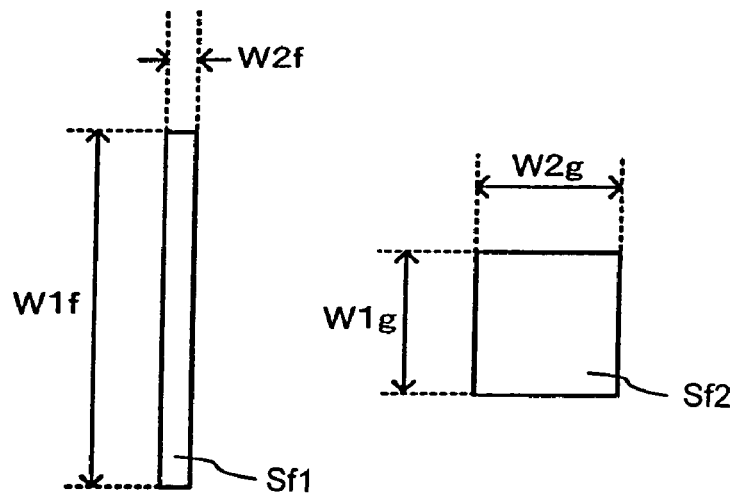
FIG. 25(a) and FIG. 25(b) show examples of the shape of the detection surfaces.
Figure 25B:
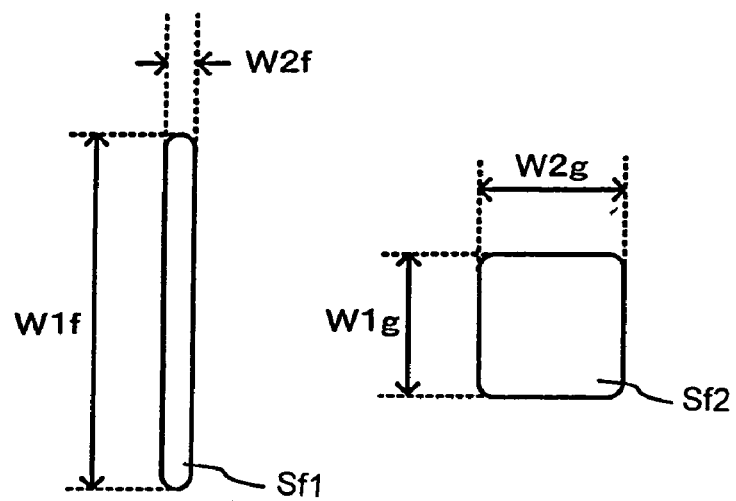

FIG. 25(*a*) and 25(*b*) show examples of the shape of the detection surface Sf1 and the detection surface Sf2. FIG. 25(*a*) shows an embodiment in which the detection surface Sf1 is oblong and the detection surface Sf2 is square, however, their four corners may be rounded as shown in FIG. 25(*b*), which is optional. The detection surface Sf1 is extended in parallel to the rotary axis of the rotary means.

When the maximum longitudinal width of detection surface Sf1 is defined as W1*f* and the maximum longitudinal width of detection surface Sf2 is W1*g*, the maximum lateral width of detection surface Sf1 is W2*f*, the maximum lateral width of the detection surface Sf2 is W2*g*, their relation is set like W1*f*>W1*g*, W2*f*<W2*g*. These longitudinal and lateral dimensions may be set by their ratio so that they may be W1*f*/W2*f*>W1*g*/W2*g*. When W2*f* is 1, W1*f* is set by the ratio of 10 or more than 10, and when W2*g* is 1, W1*g* may be set by the ratio of 3 or less than 3.

As another combination, W1*f* may be set to be 150 mm or about 150 mm±30 nm, which is most suitable for a panoramic radiography and W2*f* may be set to be 6 mm or about 10 mm±5mm, which is most suitable for panoramic radiography, W1*g* may be set to be 120 mm or about 120 mm±30 mm, which is suitable for obtaining images of a dental arch, several teeth (for example 2-8 teeth) or around ear stapes and W2*g* may be set to be 120 mm or about 120 mm±30 mm, which is suitable for obtaining images of a dental arch, several teeth for example 2-8 teeth) or around ear stapes. W1*f* also can be set to be 225 mm or about 225 mm±30 mm, then the detection surface S2 is preferably applied to both of panoramic and cephalometric radiography.

X-ray slit beam may be radiated on the X-ray detection sensor 14*b* which is an elongated electric imaging means. The irradiation field of the X-ray slit beam may be optionally formed like oblong, ellipse, or oblong with four rounded corners. Such shapes can be realized by changing the shape of the slits 12*b*, 12*c* shown in FIG. 17.

X-ray conebeam may be radiated on the X-ray detection sensor 14*a* which is a plane electric imaging means extending in two-dimensional direction. The irradiation field of X-ray conebeam may be optionally formed like circle, oblong, octagon or the like. Namely the form of the X-ray conebeam may be varied like circular cone, quadrangular pyramid, octangular pyramid or the like. For example, the shape can be realized by changing the shape of the slits 12*a* shown in FIG. 17.

When the irradiation field of the X-ray slit beam on the detection surface Sf1 is shaped so as to be the same as or substantially the same as the detection surface Sf1 by setting the slit or the irradiation field of the X-ray conebeam on the detection surface Sf2 is shaped so as to be the same as or substantially the same as the detection surface Sf2 by setting the slit, X-ray beam can be irradiated without waste.

Embodiment 3

Figure 13:
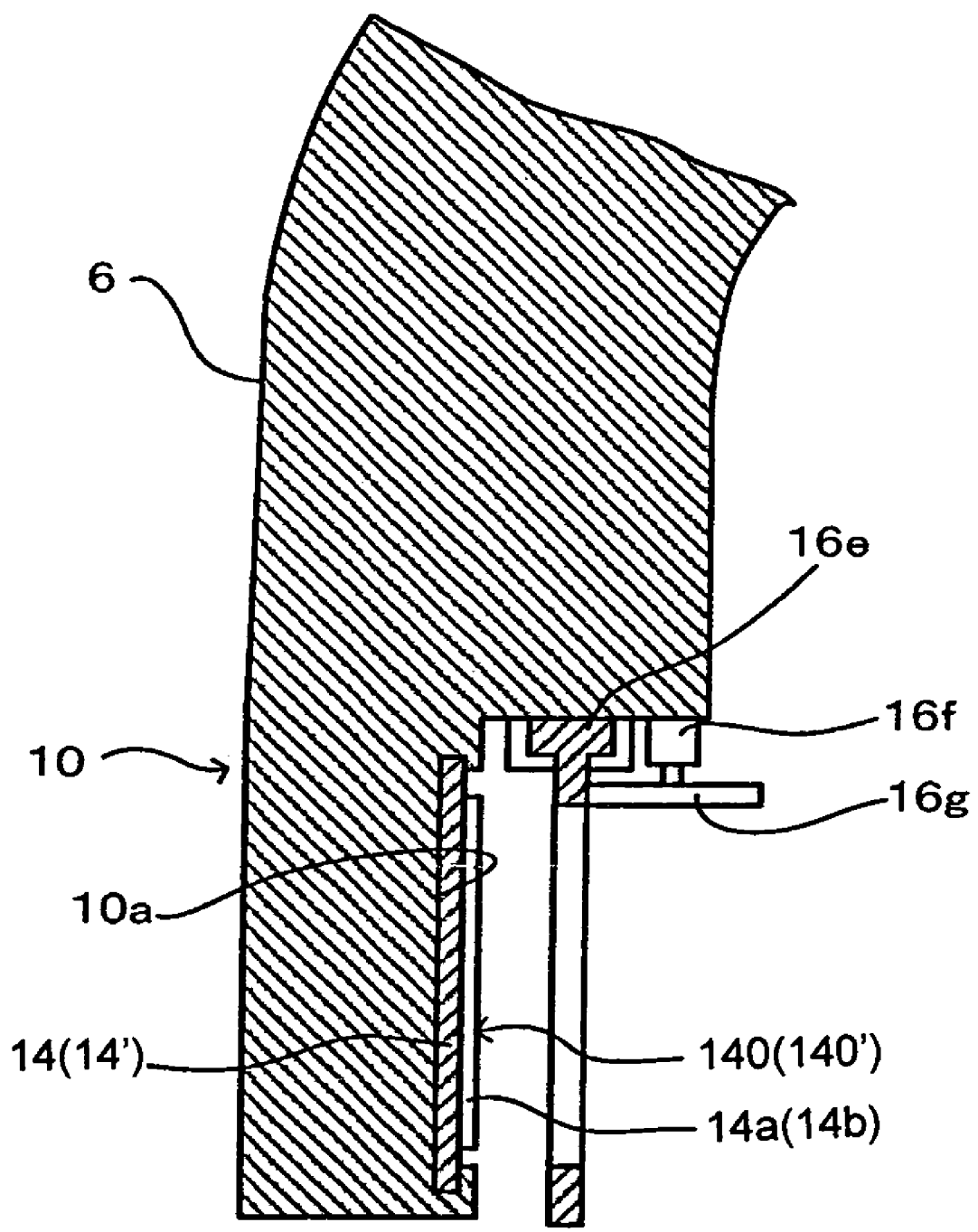
FIG. 13 is a vertical sectional view showing still other embodiment of an X-ray detecting portion.
Figure 14:
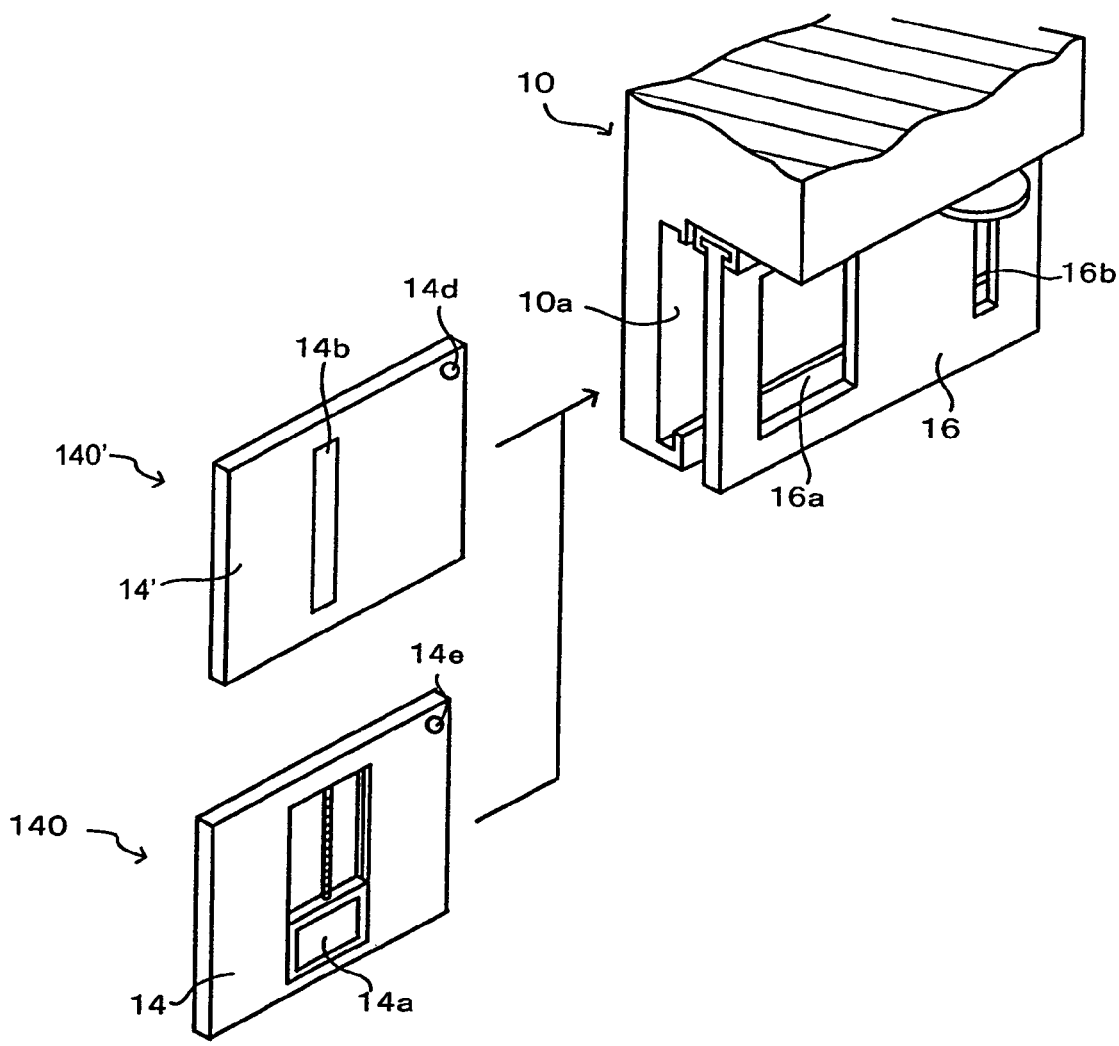
FIG. 14 is an exploded perspective view of the X-ray detecting portion of FIG. 13.

FIG. 13 and FIG. 14 show two kinds of X-ray detectors 140, 140' for which two kinds of X-ray detection sensors 14*a*, 14*b* are provided for each one of two X-ray detection sensor substrates 14, 14' respectively. The X-ray detectors 140, 140' are designed to be detachably provided for a sensor holding portion 10*a* of the X-ray detecting portion 10. The second slit board 16 formed with two kinds of second slits 16*a*, 16*b* is slidably supported in front of the sensor holding portion 10*a* via a slide mechanism 16*e*. The reference numeral 16*f* is a motor for laterally moving the second slit board 16 which is moved by rotating a rotary disc 16*g* by driving the motor 16*f*.

When each one of X-ray detectors 140, 140' is attached to the sensor holding portion 10*a*, an identifier 14*d* or 14*e* provided on each X-ray detection sensor substrate 14, 14' is detected, based on the detected information, the second slit board 16 is laterally moved by driving the motor 16*f*, then the second slits 16*a*, 16*b* corresponding to the X-ray detection sensor 14*a*, 14*b* respectively are positioned. Thereafter, each X-ray radiography mode is executed as mentioned above, so its explanation is omitted here. If the elongated X-ray detection sensor 14*b* provided for the X-ray detector 140' is about 225 mm×6 mm, the X-ray detector 140' can be also used for cephalometric radiography as mentioned above like the Embodiment 2.

Figure 15:
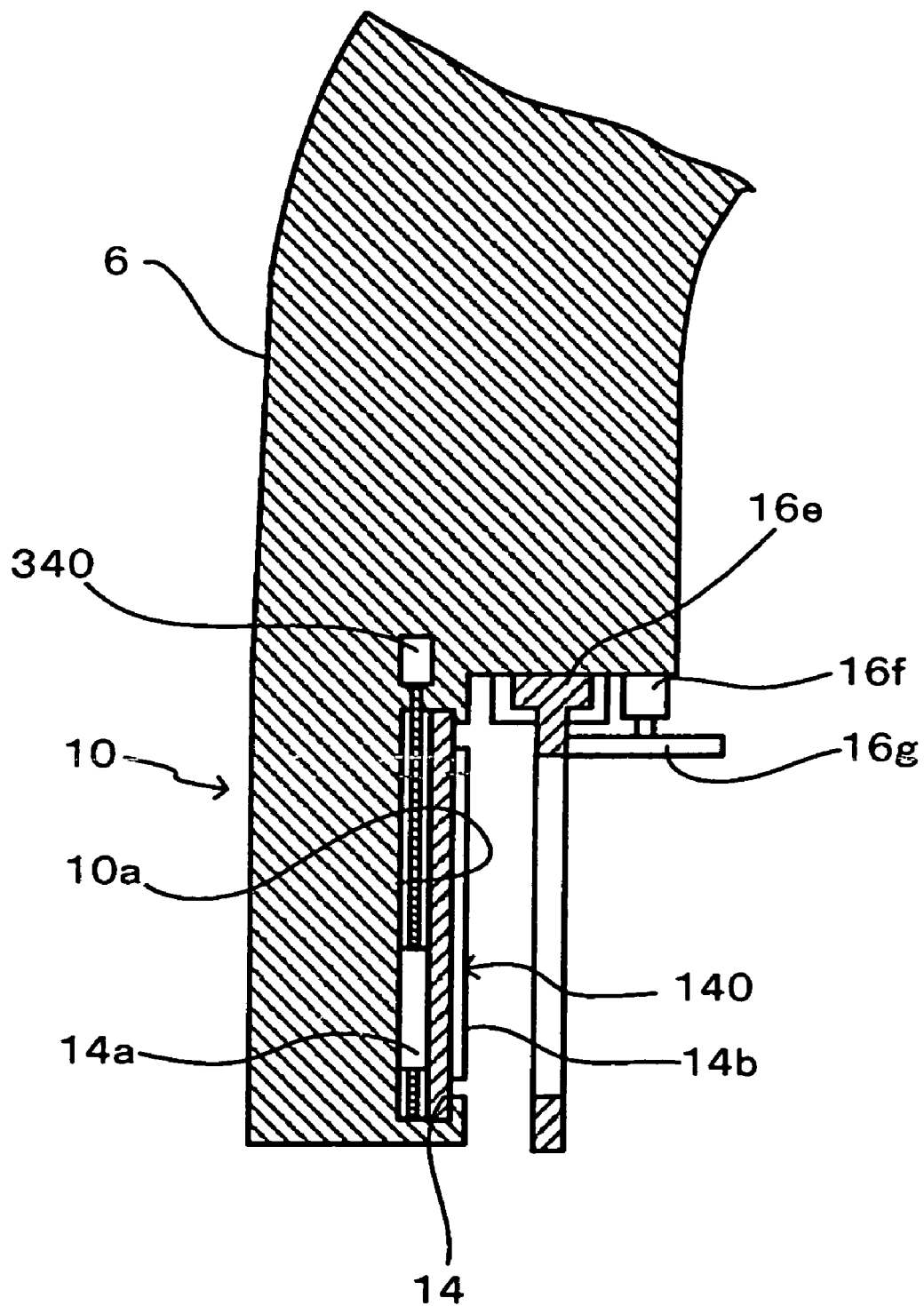
FIG. 15 is a vertical sectional view showing still other embodiment of an X-ray detecting portion.
Figure 16:
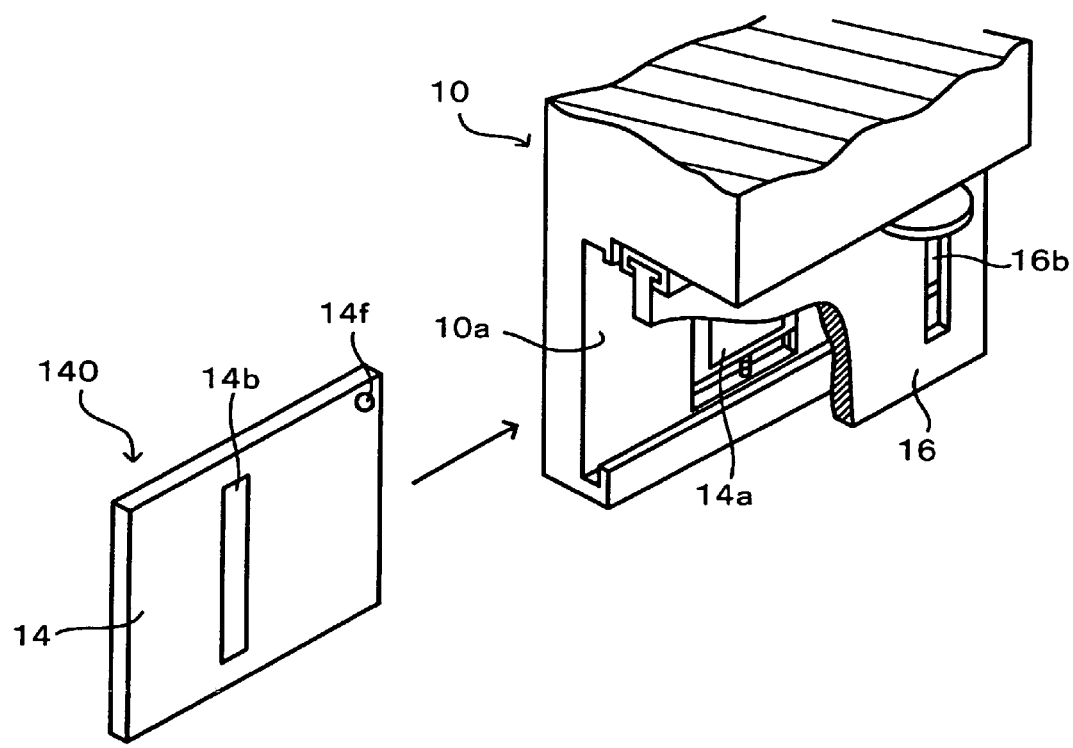
FIG. 16 is an exploded perspective view of the X-ray detecting portion of FIG. 15.

FIG. 15 and FIG. 16 show a modified embodiment of FIG. 13 and FIG. 14. These embodiments are similar to FIG. 13 and FIG. 14 in that the X-ray detector 140 has the X-ray detection sensor substrate 14 with the X-ray detection sensor 14*b* and is detachably provided to the sensor holding portion 10*a* formed at the X-ray detecting portion 10. However, they are different in that the X-ray detecting portion in FIG. 15 and FIG. 16 is constructed such that the X-ray detector 140 with the X-ray detection sensor 14*a* is integrated into the X-ray detecting portion 10 like FIG. 12.

According to the structure shown in FIG. 15 and FIG. 16, when the X-ray detector 140 formed with the X-ray detection sensor 14*b* is attached to the sensor holding portion 10*a*, the X-ray detection sensor 14*a* is hidden behind the X-ray detector 140 with the X-ray detection sensor 14*b*, thereby setting a CCD sensor mode, namely a panoramic radiography mode is set. When the X-ray detector 140 formed with the X-ray detection sensor 14*b* is detached from the sensor holding portion 10*a*, the hidden X-ray detection sensor 14*a* appears, thereby setting a MOS sensor mode, namely an X-ray CT mode is set.

The identifier 14*f* provided for the X-ray detection sensor 14*b* may be designed to detect attachment of the X-ray detector 140 with the X-ray detection sensor 14*b*.

Figure 26:
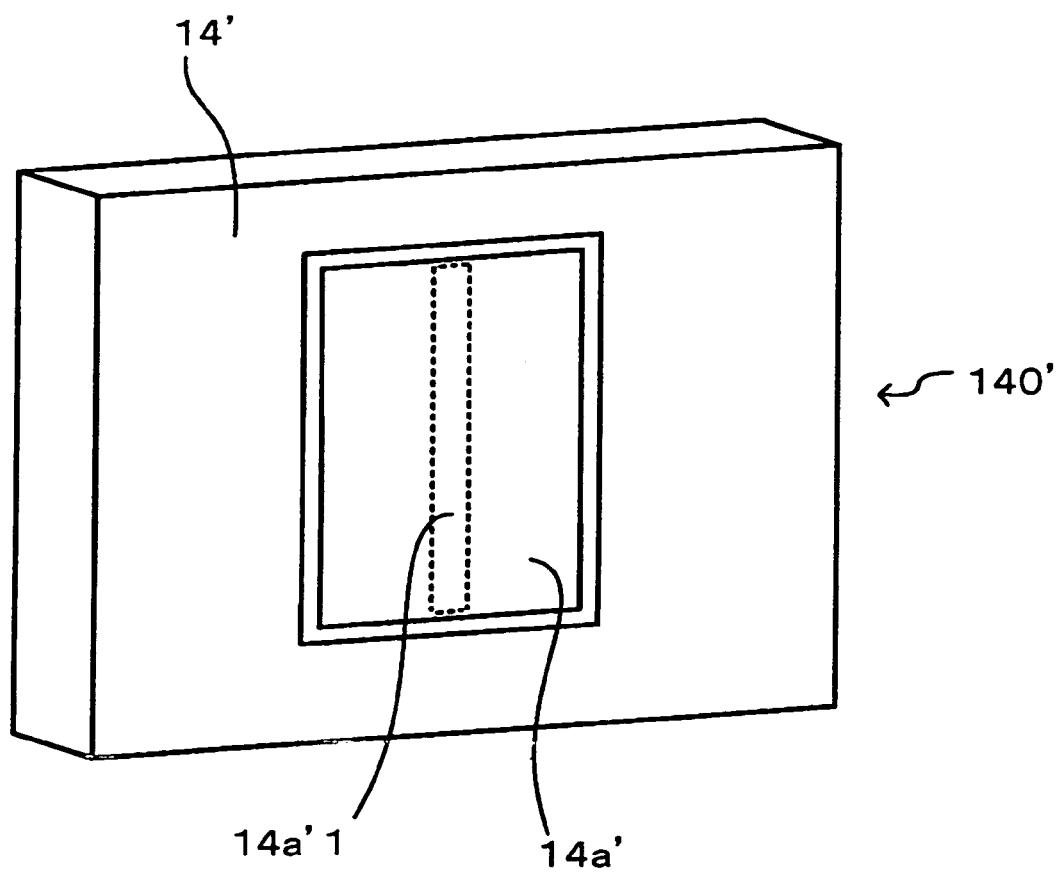
FIG. 26 shows other modified embodiment of an X-ray detector.

If the X-ray detector 140' with the X-ray detection sensor 14*a*' being a large sheet of plane electric imaging means extending in two-dimensional direction is provided for the X-ray detecting portion as shown in FIG. 19, for example, a part of the detection surface 14*a*'1 of the X-ray detection sensor 14*a*' may be activated to execute panoramic radiography with the above-mentioned X-ray slit beam as shown in FIG. 26.

Several means may be made as a plane electric imaging means extending in a two-dimensional direction and an elongated electric imaging means in the present invention. Such examples include a MOS sensor, a CMOS sensor, a TFT sensor, a CCD sensor and an X-ray solid-state image sensing device. In the present invention, the X-ray generator and the X-ray detector (or X-ray detecting portion) are moved relative to the object to be examined. On the other hand, the object may be fixed and the X-ray generator and the X-ray detector may be moved, or the X-ray generator and the X-ray detector may be fixed and the object may be moved. Namely, in the present invention, the movement of the X-ray generator and the X-ray detector relative to the object is defined as the above-mentioned relative movement.

When the X-ray generator and the X-ray detector are required to be rotated or moved relative to the object in case of obtaining tomography images, the object may be fixed and the X-ray generator and the X-ray detector may be rotated or moved or the X-ray generator and the X-ray detector may be fixed and the object may be rotated or moved. Further, the rotation or movement of object and the rotation or movement of the X-ray generator and the X-ray detector may be combined. Operations other than rotation is the same as mentioned above.

A dental X-ray imaging apparatus is explained as an example in the above-mentioned embodiments, however, the apparatus of the present invention is not limited to dentistry, but also applicable to otolaryngology, surgery and internal medicine and other medical field. The rotary arm 6 is designed to be horizontally rotated, however it may be vertically rotated around a horizontal axis to be used for tomography of torso of patient. Further, although the X-ray detection sensor 14*a* is formed as a substantial square, other shapes like rectangle or circle may be applied if it is plane extending in a two-dimensional direction. Specifically MOS is expensive, so it is economically preferable that it is formed such a shape so as to reduce the waste in case of cutting out of wafer.

While the invention has been particularly shown and described with respect to preferred embodiments thereof, it should be understood by those skilled in the art that the foregoing and other changes in form and detail may be made therein without departing from the spirit and scope of the invention as defined in the appended claims.

The invention claimed is:

1. A medical X-ray imaging apparatus comprising
a rotary means rotatable relative to an object to be examined,
an X-ray generator provided at one side of the rotary means, and
an X-ray detecting portion provided at the other side of the rotary means so as to face the X-ray generator,
wherein an X-ray detector is provided in said X-ray detecting portion or is detachably mounted in said X-ray detecting portion, and
said X-ray detector is provided with an imaging portion comprised of a plane electric imaging means extending in a two-dimensional direction to detect an X-ray cone beam used for X-ray CT,
and an imaging portion positioning means for moving up and down said imaging portion in said X-ray detector,
and wherein said medical X-ray imaging apparatus is further provided with a mode switching means for selecting a panoramic radiography mode and an X-ray CT mode, wherein an X-ray slit beam for panoramic radiography is irradiated in said panoramic radiography mode and said X-ray cone beam for said X-ray CT is irradiated in said X-ray CT mode,
and wherein said X-ray generator is further provided with an irradiating direction changing means for changing the irradiating direction of the X-ray cone beam for said X-ray CT to be emitted up and down therefrom corresponding to a position of said imaging portion in said X-ray CT mode by moving up and down a slit for forming an X-ray beam as said X-ray cone beam for X-ray CT positioned at an X-ray radiation port of said X-ray generator.

2. The medical X-ray imaging apparatus set forth in claim 1, wherein said imaging portion positioning means is so constructed as to move up and down said imaging portion by a motor.

3. The medical X-ray imaging apparatus as set forth in claim 1, wherein said imaging portion positioning means moves said imaging portion up and down stepwisely relative to an objective imaging region of the object to be examined.

4. The medical X-ray imaging apparatus as set forth in claim 1, wherein said X-ray detector comprises said plane electric imaging means and an elongated electric imaging means.

5. The medical X-ray imaging apparatus as set forth in claim 4, wherein said plane electric imaging means and said elongated electric imaging means are provided on one side of an X-ray detection sensor substrate.

6. The medical X-ray imaging apparatus as set forth in claim 1, wherein said plane electric imaging means is any one of a MOS sensor, a CMOS sensor, a TFT sensor, a CCD sensor and an X-ray solid-state image sensing device.

7. The medical X-ray imaging apparatus as set forth in claim 4, wherein said elongated electric imaging means is any one of a MOS sensor, a CMOS sensor, a TFT sensor, a CCD sensor and an X-ray solid-state image sensing device.

8. The medical X-ray imaging apparatus
as set forth in claim 4 or 5
wherein said X-ray detecting portion is constructed such that said plane electric imaging means and said elongated electric imaging means are selectively used by being shifted, attached or detached thereto, depending on the change of radiography mode.

9. The medical X-ray imaging apparatus as set forth in claim 8, wherein
said medical X-ray imaging apparatus further executes panoramic radiography, and
said plane electric imaging means of said X-ray detector is used in an X-ray CT mode, whereas said elongated electric imaging means is used in a panoramic radiography mode.

10. A medical X-ray imaging apparatus comprising a rotary means rotatable relative to an object to be examined, an X-ray generator provided at one side of the rotary means, and an X-ray detecting portion provided at the other side of the rotary means so as to face the X-ray generator, wherein
said X-ray detecting portion is provided with an X-ray detector having therein an imaging portion comprised of a plane electric imaging means extending in a two-dimensional direction to detect an X-ray cone beam used for X-ray CT with a detection area enough to detect the X-ray cone beam for said X-ray CT without moving in the X-ray detecting portion for X-ray CT or said X-ray detecting portion is so constructed as to detachably mount said X-ray detector therein, and
said X-ray imaging apparatus is further provided with a mode switching means for selecting a panoramic radiography is irradiated in said panoramic wherein a X-ray slit beam for panoramic radiography is irradiated in said panoramic radiography mode and said X-ray cone beam for said X-ray CT is irradiated in said X-ray CT mode, and wherein said X-ray generator comprises an irradiation field changing means for changing the placement of the irradiation field defined by said X-ray cone beam for said X-ray CT to be irradiated partially on the imaging portion of said electric imaging means up and down in said X-ray CT mode by moving up and down a slit for forming an X-ray beam as said X-ray cone beam for X-ray CT positioned at an X-ray radiation port of said X-ray generator.

11. The medical X-ray imaging apparatus as set forth in claim 10, wherein said medical X-ray imaging apparatus further executes panoramic radiography, and said plane electric imaging means is used for a panoramic radiography mode depending on the change of radiography mode into panoramic radiography mode.

12. The medical X-ray imaging apparatus as set forth in claim 1 or 10, further comprising a two-dimensional position control means for controlling position of at least said rotary means or said object in two-dimensional direction defined by an X-axis direction and a Y-axis direction in three-dimensional axial directions defined by an X-axis, a Y-axis, and a Z-axis, where the Z-axis is defined as up and down direction of said imaging portion and both of said x-axis and said Y-axis are normal to said Z-axis.

13. The medical X-ray imaging apparatus as set forth in claim 1 or 10, comprising an object holding means with an object fixing means for holding the object to be examined, and an object shifting means for tilting and/or elevating said object fixing means relative to said object holding means.

14. The medical X-ray imaging apparatus as set forth in claim 1 or 10, comprising a support for said rotary means, an elevating guide portion for guiding to move up and down said support, and an object holding means for holding the object to be examined thereon, wherein said support is capable of being independently shifted relative to said elevating guide portion.

15. The medical X-ray imaging apparatus as set forth in claim 14 wherein said object holding means comprises an object fixing means for fixing the object to be examined therewith and an object shifting means for tilting and/or elevating said object fixing means relative to said object holding means.

16. A medical X-ray imaging apparatus comprising a rotary means rotatable relative to an object to be examined, an X-ray generator provided at one side of the rotary means, and an X-ray detecting portion provided at the other side of the rotary means so as to face the X-ray generator, and a mode switching means for selecting a panoramic radiography mode and an X-ray CT mode, wherein an X-ray slit beam for panoramic radiography is irradiated in said panoramic radiography mode and an X-ray cone beam for X-ray CT is irradiated in said X-ray CT mode, and wherein said X-ray detecting portion is provided with an X-ray detector having therein an imaging portion comprised of a plane electric imaging means extending in a two-dimensional direction to detect said X-ray cone beam used for X-ray CT with a detection area enough to detect the X-ray cone beam for said X-ray CT without moving in the X-ray detecting portion for X-ray CT or said X-ray detecting portion is so constructed as to detachably mount said X-ray detector therein, and said X-ray generator comprises an irradiation field changing means for changing the placement of the irradiation field defined by said X-ray cone beam for said X-ray CT to be irradiated partially on the imaging portion of said electric imaging means up and down in said X-ray CT mode by moving up and down a slit for forming an X-ray beam as said X-ray cone beam for X-ray CT positioned at an X-ray radiation port of said X-ray generator, and wherein said medical X-ray imaging apparatus further comprises a two-dimensional position control means for controlling position of at least said rotary means or said object in two-dimensional direction normal to up and down direction of the placement of the irradiation field on said imaging portion.

17. The medical X-ray imaging apparatus according to claim 1, wherein said medical X-ray imaging apparatus is further provided with a slit for panoramic radiography, and said slit for X-ray CT is positioned at the X-ray radiation port of said X-ray generator when the X-ray CT mode is selected, and said slit for panoramic radiography is positioned at the X-ray radiation port of said X-ray generator when the panoramic radiography is selected.

18. The medical X-ray imaging apparatus according to claim 1, wherein a slit for panoramic radiography is further provided in a slit board, and said slit for X-ray CT is positioned at the X-ray radiation port of said X-ray generator when the X-ray CT mode is selected, and said slit for panoramic radiography is positioned at the X-ray radiation port of said X-ray generator when the panoramic radiography mode is selected.

19. The medical X-ray imaging apparatus according to claim 1, wherein a height of said plane electric imaging means for X-ray CT is controlled without changing a position of a patient.

* * * * *

UNITED STATES PATENT AND TRADEMARK OFFICE
CERTIFICATE OF CORRECTION

| | | |
|---|---|---|
| PATENT NO. | : 7,577,232 B2 | Page 1 of 1 |
| APPLICATION NO. | : 11/407504 | |
| DATED | : August 18, 2009 | |
| INVENTOR(S) | : Akifumi Tachibana et al. | |

It is certified that error appears in the above-identified patent and that said Letters Patent is hereby corrected as shown below:

The third paragraph of claim 10 is corrected to read as follows:

said medical X-ray imaging apparatus is further provided with a mode switching means for selecting a panoramic radiography mode and an X-ray CT mode, wherein an X-ray slit beam for panoramic radiography is irradiated in said panoramic radiography mode and said X-ray cone beam for said X-ray CT is irradiated in said X-ray CT mode, and wherein Signed and Sealed this
First Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,577,232 B2
APPLICATION NO. : 11/407504
DATED : August 18, 2009
INVENTOR(S) : Akifumi Tachibana et al.

Page 1 of 1

It is certified that error appears in the above-identified patent and that said Letters Patent is hereby corrected as shown below:

Column 18, line 64 - Column 19, line 3, the third paragraph of claim 10 is corrected to read as follows:

said medical X-ray imaging apparatus is further provided with a mode switching means for selecting a panoramic radiography mode and an X-ray CT mode, wherein an X-ray slit beam for panoramic radiography is irradiated in said panoramic radiography mode and said X-ray cone beam for said X-ray CT is irradiated in said X-ray CT mode, and wherein This certificate supersedes the Certificate of Correction issued February 1, 2011.

Signed and Sealed this
First Day of March, 2011

David J. Kappos
*Director of the United States Patent and Trademark Office*